US009217697B2

(12) United States Patent
U'Ren et al.

(10) Patent No.: US 9,217,697 B2
(45) Date of Patent: *Dec. 22, 2015

(54) APPARATUS, SYSTEM, AND METHOD FOR COLLECTING A TARGET MATERIAL

(71) Applicant: RareCyte, Inc., Seattle, WA (US)

(72) Inventors: Lance U'Ren, Seattle, WA (US); Jennifer Chow, Seattle, WA (US)

(73) Assignee: RARECYTE, INC., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/665,368

(22) Filed: Mar. 23, 2015

(65) Prior Publication Data

US 2015/0192506 A1     Jul. 9, 2015

Related U.S. Application Data

(63) Continuation-in-part of application No. 14/610,522, filed on Jan. 30, 2015, which is a continuation-in-part of application No. 14/495,449, filed on Sep. 24, 2014, now Pat. No. 9,039,999, which is a (Continued)

(51) Int. Cl.
*G01N 1/40*     (2006.01)
*G01N 33/49*     (2006.01)
*C12Q 1/68*     (2006.01)
*B01L 3/00*     (2006.01)

(Continued)

(52) U.S. Cl.
CPC ............ *G01N 1/4077* (2013.01); *B01L 3/5021* (2013.01); *B01L 3/50215* (2013.01); *B01L 3/5635* (2013.01); *B03D 3/00* (2013.01); *C12Q 1/6806* (2013.01); *G01N 33/491* (2013.01); *B01D 21/262* (2013.01); *B01L 9/50* (2013.01); *B01L 2200/026* (2013.01); *B01L 2300/0672* (2013.01); *B01L 2300/0851* (2013.01); *B01L 2400/0683* (2013.01); *Y10T 436/25375* (2015.01)

(58) Field of Classification Search
CPC ............... G01N 1/4077; G01N 33/491; B01L 3/50215; B01L 3/5635; B01L 3/5021; B01L 3/502; B01L 2300/0851; B01L 9/50; B01L 2200/026; B01L 2400/0683; B01L 2300/0672; B03D 3/00; C12Q 1/6806; B01D 21/262
See application file for complete search history.

(56) References Cited

U.S. PATENT DOCUMENTS 3,873,271 A * 3/1975 Young ................ G01N 33/2847
                                                          206/524.8
4,464,254 A     8/1984   Dojki et al.

(Continued)

FOREIGN PATENT DOCUMENTS

WO     WO9712681     *    4/1997          B01L 3/14

*Primary Examiner* — Lore Jarrett

(57) ABSTRACT

This disclosure is directed to an apparatus, system and method for retrieving target material from a suspension. A system includes a processing vessel, such as an Eppendorf tube, a syringe or a test tube, and a collector. The collector is sized and shaped to fit into a primary vessel, such as a test tube. The collector funnels the target material from the suspension through a cannula and into the processing vessel. The cannula extends into a cavity at a first end of the collector that holds the processing vessel. The collector includes a concave opening at a second end in fluid communication with the cannula. In one implementation, the processing vessel includes at least one displacement fluid to be expelled, such that the at least one displacement fluid pushes the target material into the collector.

20 Claims, 24 Drawing Sheets

Related U.S. Application Data continuation-in-part of application No. 14/090,337, filed on Nov. 26, 2013, which is a continuation-in-part of application No. 14/266,939, filed on May 1, 2014.

(60) Provisional application No. 61/935,457, filed on Feb. 4, 2014, provisional application No. 61/869,866, filed on Aug. 26, 2013, provisional application No. 61/818,301, filed on May 1, 2013, provisional application No. 61/791,883, filed on Mar. 15, 2013, provisional application No. 61/745,094, filed on Dec. 21, 2012, provisional application No. 61/732,029, filed on Nov. 30, 2012.

(51) Int. Cl.
  *B03D 3/00* (2006.01)
  *B01D 21/26* (2006.01)
  *B01L 9/00* (2006.01)

(56) References Cited

U.S. PATENT DOCUMENTS

| | | |
|---|---|---|
| 5,186,824 A | 2/1993 | Anderson et al. |
| 5,254,312 A * | 10/1993 | Staebler ............... B01L 3/0293 422/501 |
| 5,275,933 A | 1/1994 | Teng et al. |
| 5,282,981 A | 2/1994 | Adams et al. |
| 5,393,674 A | 2/1995 | Levine et al. |
| 5,437,987 A | 8/1995 | Tens et al. |
| 5,489,386 A | 2/1996 | Saunders et al. |
| 5,840,502 A | 11/1998 | Van Vlasselaer |
| 5,866,071 A | 2/1999 | Leu |
| 5,962,237 A | 10/1999 | Ts'o et al. |
| 7,456,024 B2 | 11/2008 | Dahm et al. |
| 8,110,393 B2 | 2/2012 | Aparicio et al. |
| 8,278,118 B2 | 10/2012 | Horn et al. |
| 2004/0038356 A1 | 2/2004 | Pertoft et al. |
| 2004/0247487 A1 | 12/2004 | Commercon et al. |
| 2005/0014273 A1 * | 1/2005 | Dahm .................... B01J 19/249 436/45 |
| 2007/0272612 A1 | 11/2007 | Horn et al. |
| 2011/0124106 A1 | 5/2011 | Froman et al. |
| 2011/0251041 A1 * | 10/2011 | Chavarria ........... A61M 1/3693 494/4 |
| 2013/0072402 A1 | 3/2013 | Takamura et al. |
| 2013/0280693 A1 | 10/2013 | Mace et al. |

\* cited by examiner

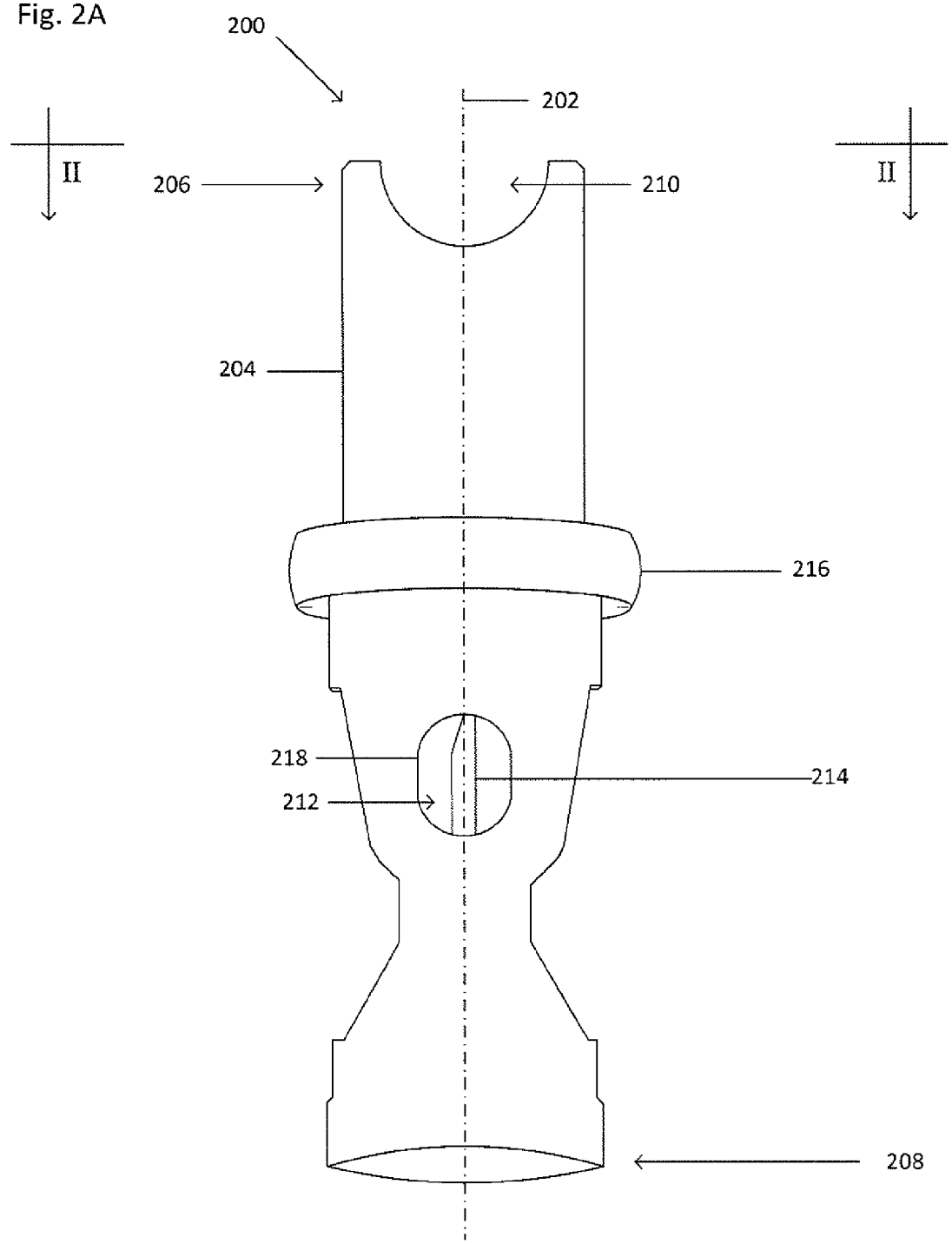

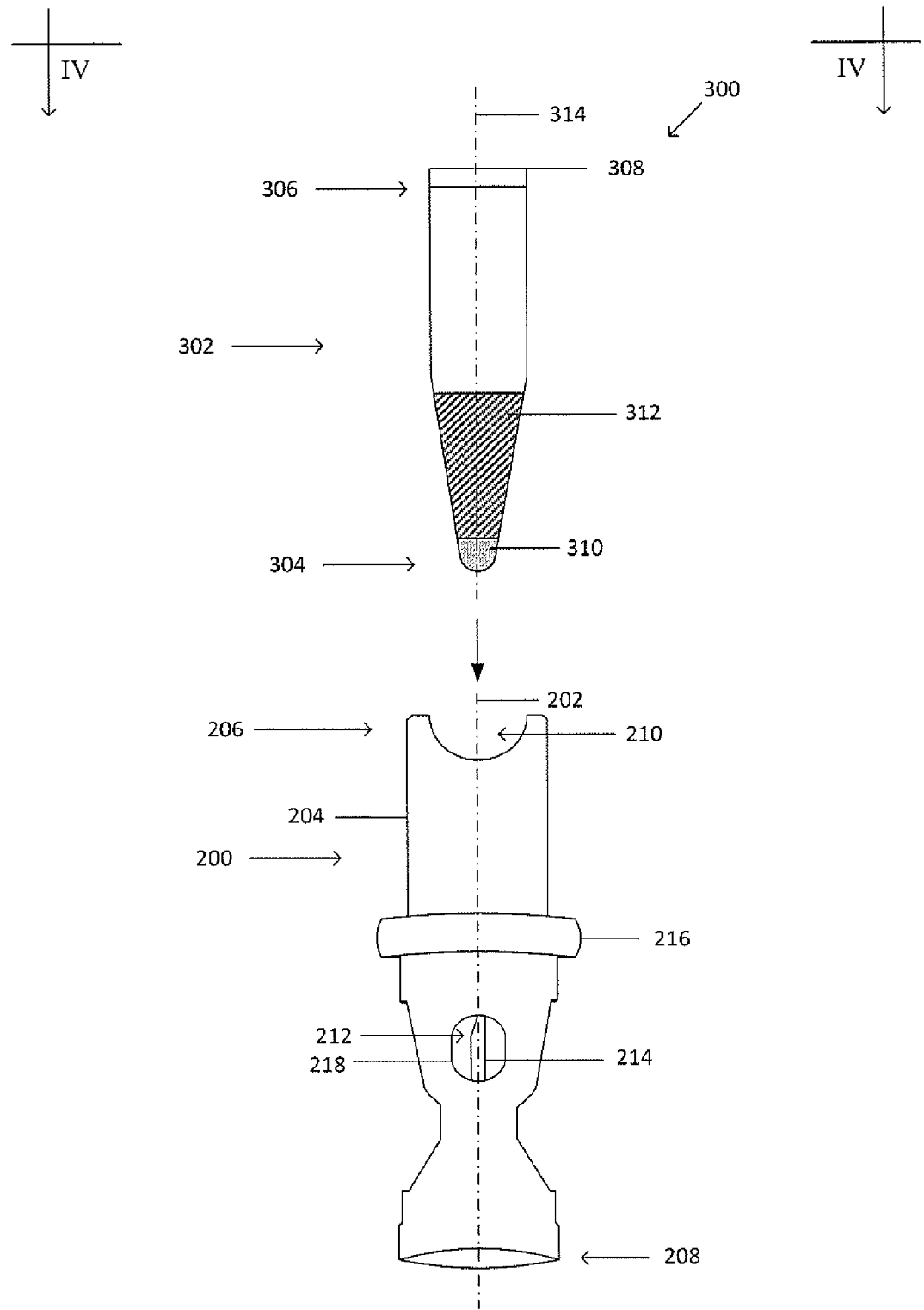

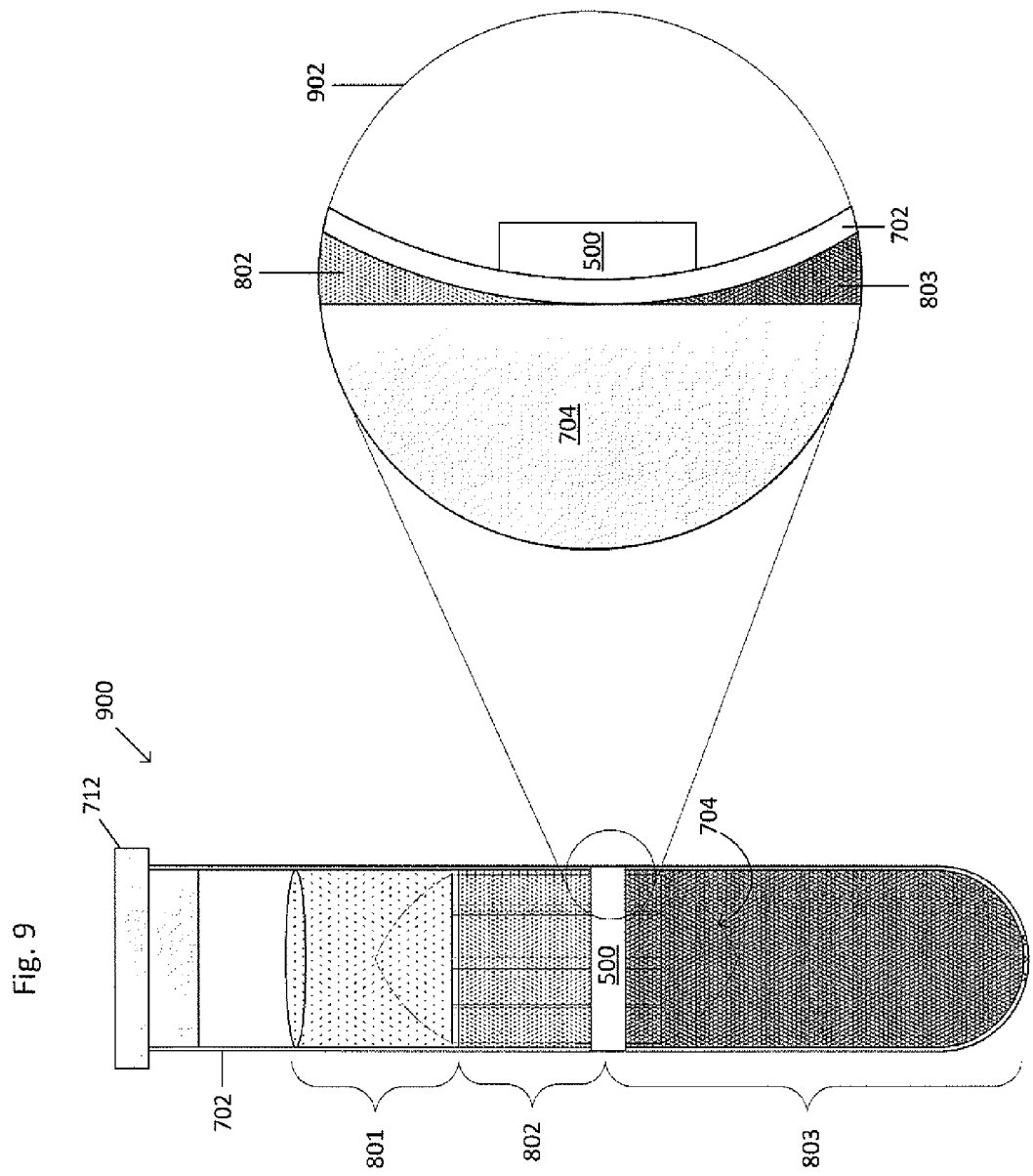

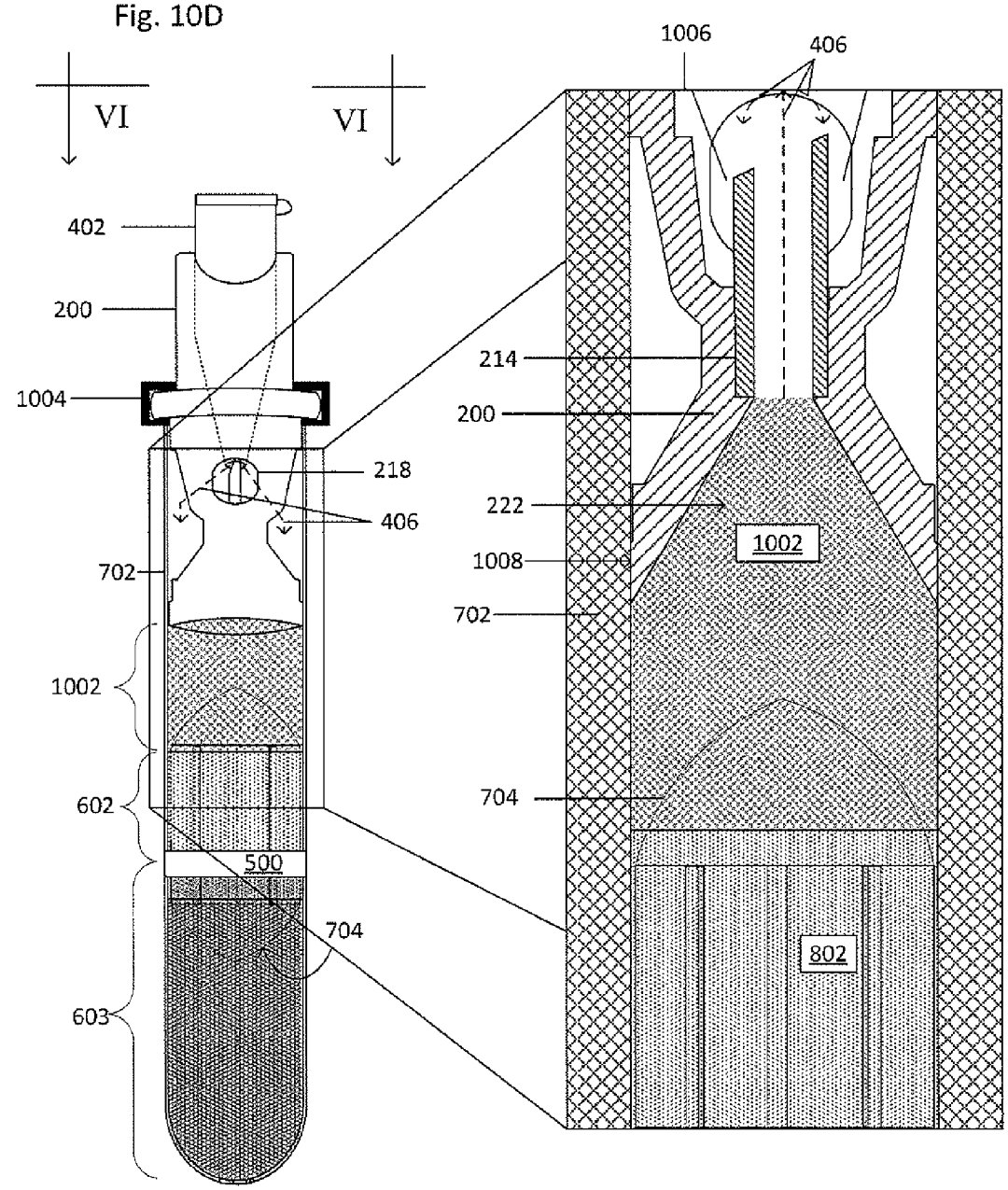

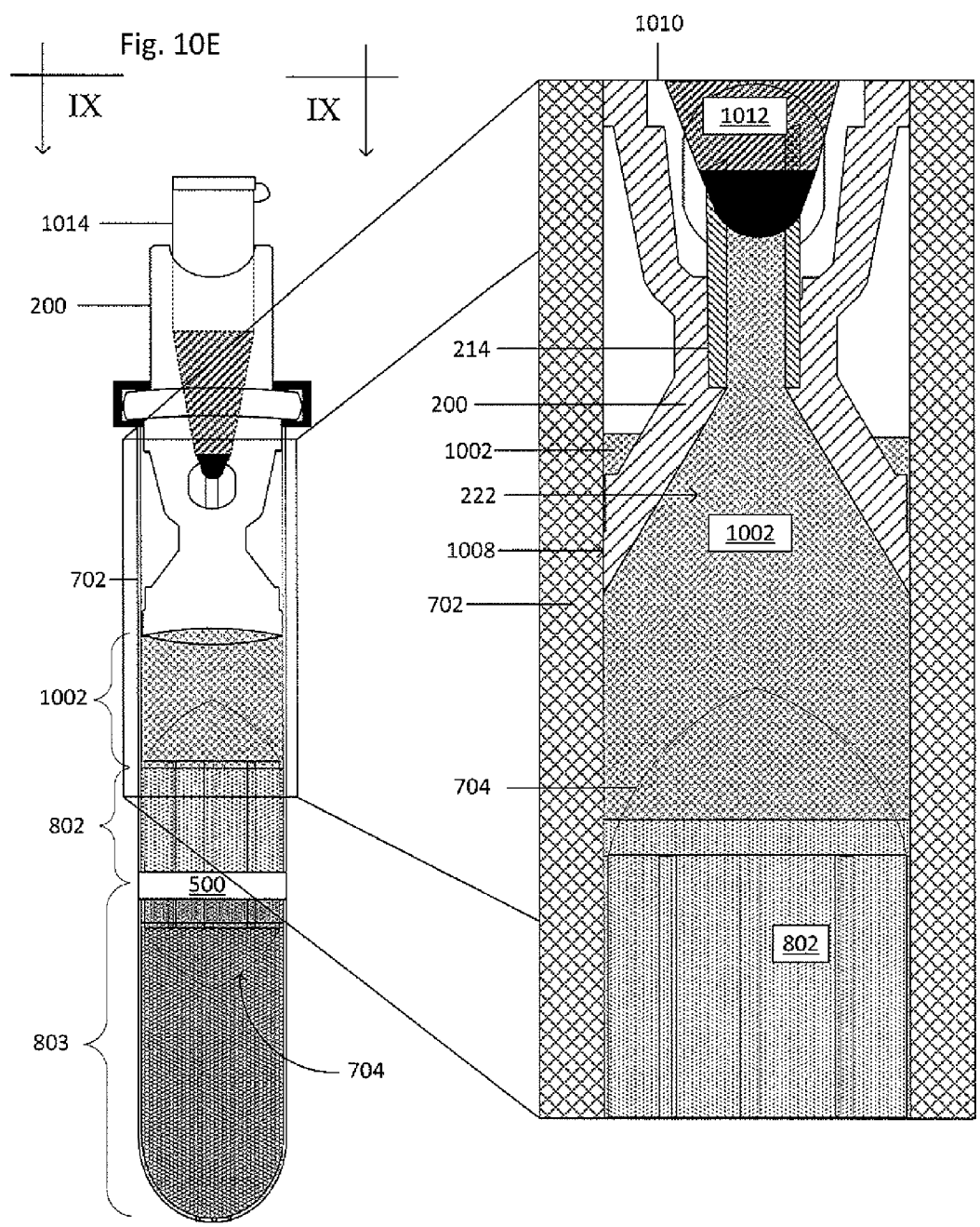

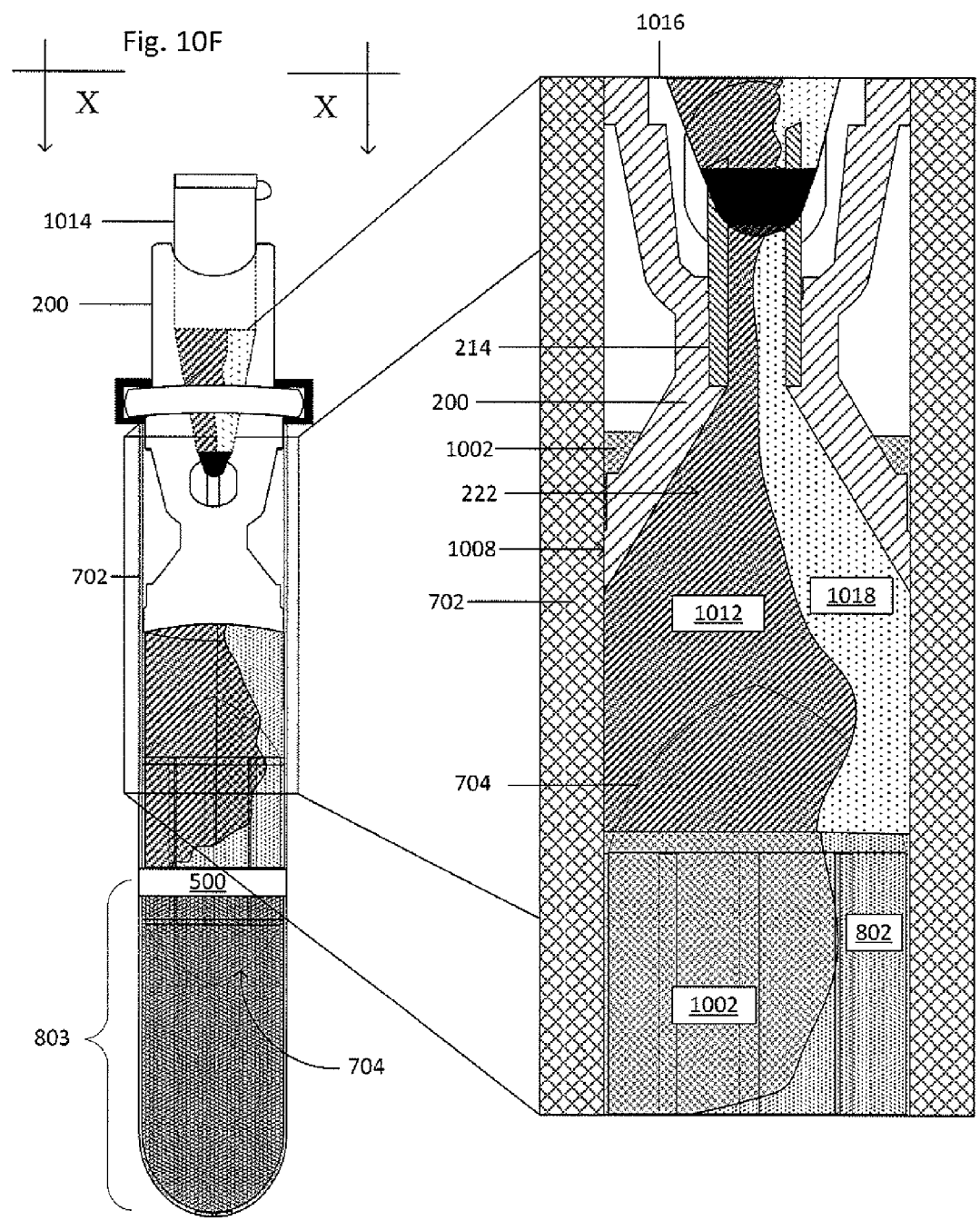

APPARATUS, SYSTEM, AND METHOD FOR COLLECTING A TARGET MATERIAL

CROSS-REFERENCE TO A RELATED APPLICATION

This application is a continuation-in-part of application Ser. No. 14/610,522, filed Jan. 30, 2015, which claims the benefit of Provisional Application No. 61/935,457, filed Feb. 4, 2014, and which is also a continuation-in-part of application Ser. No. 14/495,449, filed Sep. 24, 2014, which is a continuation-in-part of application Ser. No. 14/090,337, filed Nov. 26, 2013, which claims the benefit of Provisional Application No. 61/732,029, filed Nov. 30, 2012; Provisional Application No. 61/745,094, filed Dec. 21, 2012; Provisional Application No. 61/791,883, filed Mar. 15, 2013; Provisional Application No. 61/818,301, filed May 1, 2013; and Provisional Application No. 61/869,866, filed Aug. 26, 2013, and which is also a continuation-in-part of application Ser. No. 14/266,939, filed May 1, 2014, which claims the benefit of Provisional Application No. Provisional Application No. 61/818,301, filed May 1, 2013, Provisional Application No. 61/869,866, filed Aug. 26, 2013, and Provisional Application No. 61/935,457, filed Feb. 4, 2014.

TECHNICAL FIELD

This disclosure relates generally to density-based fluid separation and, in particular, to retrieving fetal material from a suspension.

BACKGROUND

Suspensions often include materials of interests that are difficult to detect, extract and isolate for analysis. For instance, whole blood is a suspension of materials in a fluid. The materials include billions of red and white blood cells and platelets in a proteinaceous fluid called plasma. Whole blood is routinely examined for the presence of abnormal organisms or cells, such as ova, fetal cells, endothelial cells, parasites, bacteria, and inflammatory cells, and viruses, including HIV, cytomegalovirus, hepatitis C virus, and Epstein-Barr virus. Currently, practitioners, researchers, and those working with blood samples try to separate, isolate, and extract certain components of a peripheral blood sample for examination. Typical techniques used to analyze a blood sample include the steps of smearing a film of blood on a slide and staining the film in a way that enables certain components to be examined by bright field or fluorescence microscopy.

On the other hand, materials of interest that occur in a suspension with very low concentrations are especially difficult if not impossible to detect and analyze using many existing techniques. As a result, practitioners, researchers, and those working with suspensions continue to seek systems and methods for accurate analysis of suspensions for the presence or absence rare materials of interest.

DESCRIPTION OF THE DRAWINGS

FIGS. 2A-2B show an example collector.
FIGS. 3A-3B show an example collector-processing vessel system.
FIG. 9 shows an example sealing ring and the example float and primary vessel system forming a seal.
FIGS. 10A-10G show an example system retrieving a target material.

DETAILED DESCRIPTION

This disclosure is directed to an apparatus, system and method for retrieving target material from a suspension. A system includes a processing vessel, such as an Eppendorf tube, a syringe or a test tube, and a collector. The collector is sized and shaped to fit into a primary vessel, such as a test tube. The collector funnels the target material from the suspension through a cannula and into the processing vessel. The cannula extends into a cavity at a first end of the collector that holds the processing vessel. The collector includes a concave opening at a second end in fluid communication with the cannula. In one implementation, the processing vessel includes at least one displacement fluid to be expelled, such that the at least one displacement fluid pushes the target material into the collector.

Collector

Figure 1A:
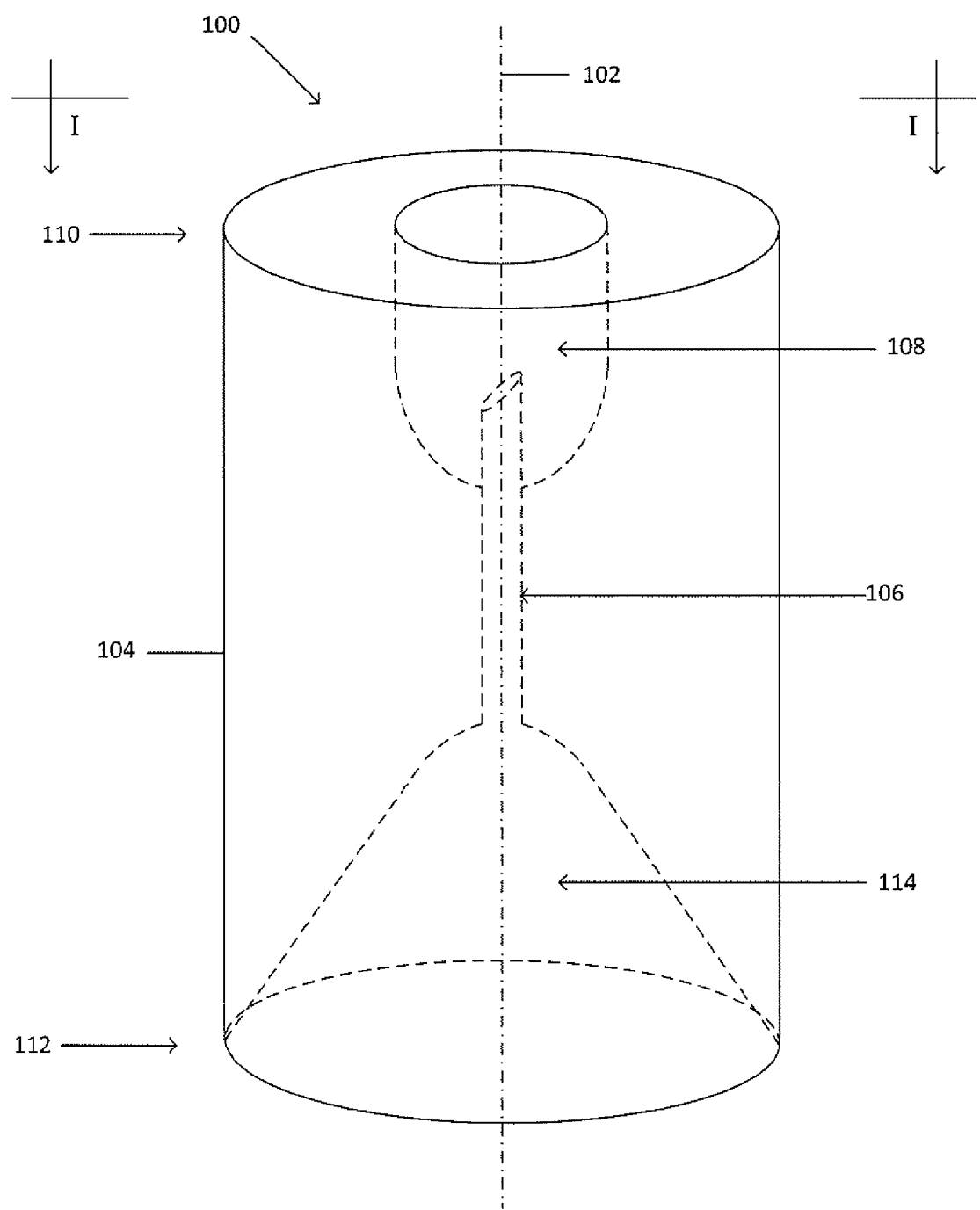
FIGS. 1A-1B show an example collector.
Figure 1B:
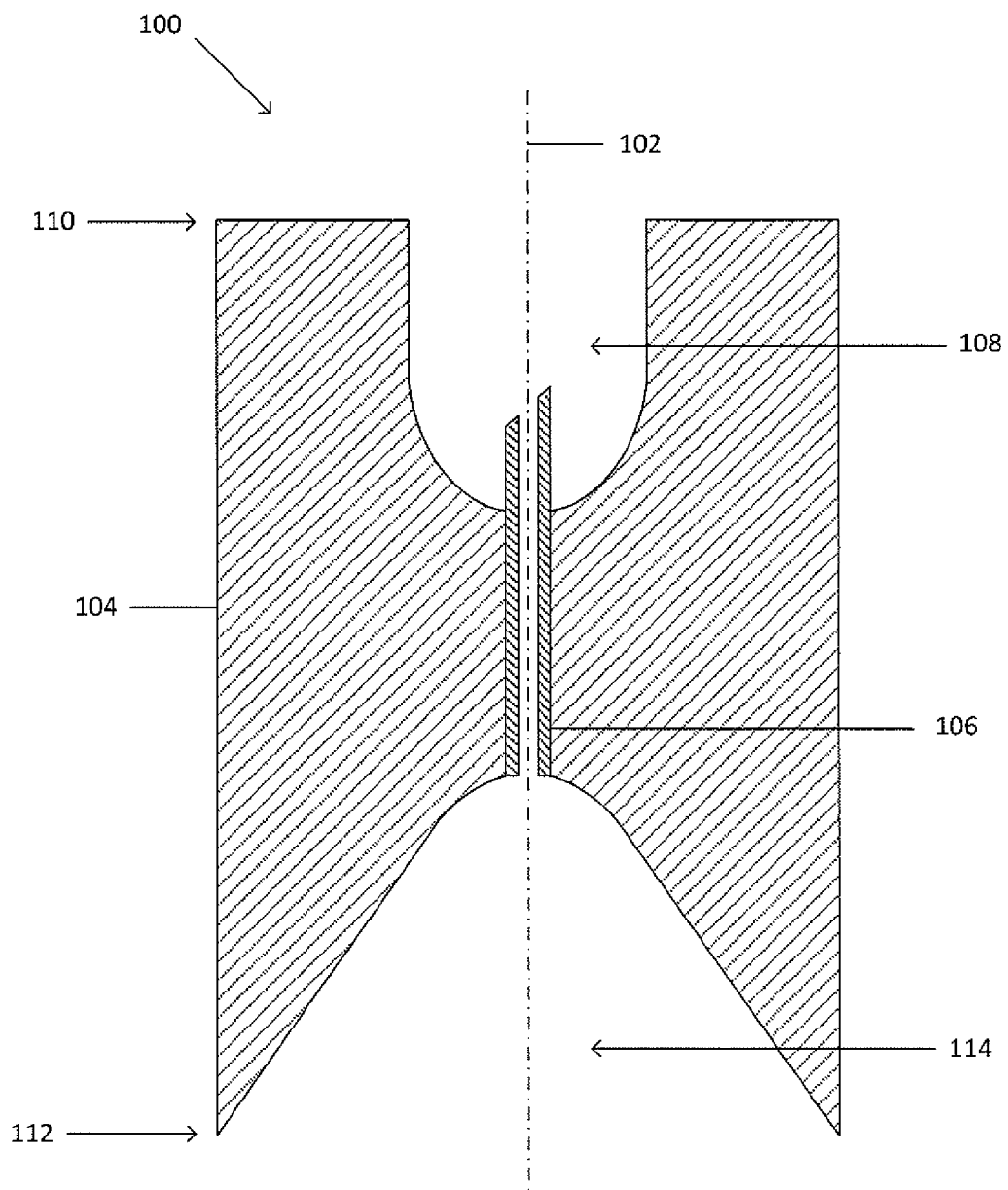

FIG. 1A shows an isometric view of a collector 100. FIG. 1B shows a cross-sectional view of the collector 100 taken along the line I-I shown in FIG. 1A. Dot-dashed line 102 represents the central or highest-symmetry axis of the collector 100. The collector 100 may be sized and shaped to fit within a primary vessel containing or capable of holding a suspension, the suspension suspected of including target material. The collector 100 funnels the target material from the suspension through a cannula 106 and into a processing vessel (not shown) to be located within a cavity 108. The collector 100 includes the main body 104 which includes a first end 110 and a second end 112. A seal may be formed between the second end 112 and an inner wall of the primary vessel to maintain a fluid-tight sealing engagement before, during, and after centrifugation and to inhibit any portion of the suspension from being located or flowing between an inner wall of the primary vessel and a main body 104 of the collector 100. The seal may be formed by an interference fit, a grease (such as vacuum grease), an adhesive, an epoxy, by bonding (such as by thermal bonding), by welding (such as by ultrasonic welding), by clamping (such as with a ring or clamp), an insert (such as an O-ring or a collar) that fits between the second end 112 and the inner wall of the primary vessel, or the like. The main body 104 may be any appropriate shape, including, but not limited to, cylindrical, triangular, square, rectangular, or the like. The collector 100 also includes an internal concave opening 114 which tapers toward the cannula 106 from the second end 112. The concave opening 114 channels target material from below the second end 112 into the cannula 106 which is connected to, and in fluid communication with, an apex of the concave opening 114. The apex of the concave opening 114 has a smaller diameter than the mouth of the concave opening 114. The concave opening 114 is formed by a tapered wall that may be straight, curvilinear, arcuate, or the like. The concave opening 114 may be any appropriate shape, including, but not limited to, tubular, spherical, domed, conical, rectangular, pyramidal, or the like. Furthermore, the outermost diameter or edge of the concave opening 114 may be in continuous communication or constant contact (i.e. sit flush) with the inner wall of the primary vessel such that no dead space is present between the second end 112 of the collector 100 and the inner wall of the primary vessel.

The cannula 106, such as a tube or a needle, including, but not limited to a non-coring needle, extends from the apex of the concave opening 114 and into the cavity 108. In the example of FIG. 1, the cavity 108 is a concave opening extending from the first end 110 into the main body 104 and may accept and support the processing vessel (not shown). The cavity 108 may be any appropriate depth to accept and support the processing vessel (not shown). The cannula 106 may extend any appropriate distance into the cavity 108 in order to puncture the base of, or be inserted into, the processing vessel (not shown). The cannula 106 may include a flat tip, a beveled tip, a sharpened tip, or a tapered tip. Furthermore, the cavity 108 may be any appropriate shape, including, but not limited to, tubular, spherical, domed, conical, rectangular, pyramidal, or the like. The cavity 108 may be threaded to engage a threaded portion of the processing vessel (not shown).

The collector 100 may also include a retainer (not shown) to prevent the collector 100 from sliding relative to the primary vessel, thereby keeping the collector 100 at a pre-determined height within the primary vessel. The retainer (not shown) may be a shoulder extending radially from the first end 110, a clip, a circular protrusion that extends beyond the circumference of the cylindrical main body 104, a detent, or the like.

Figure 2B:
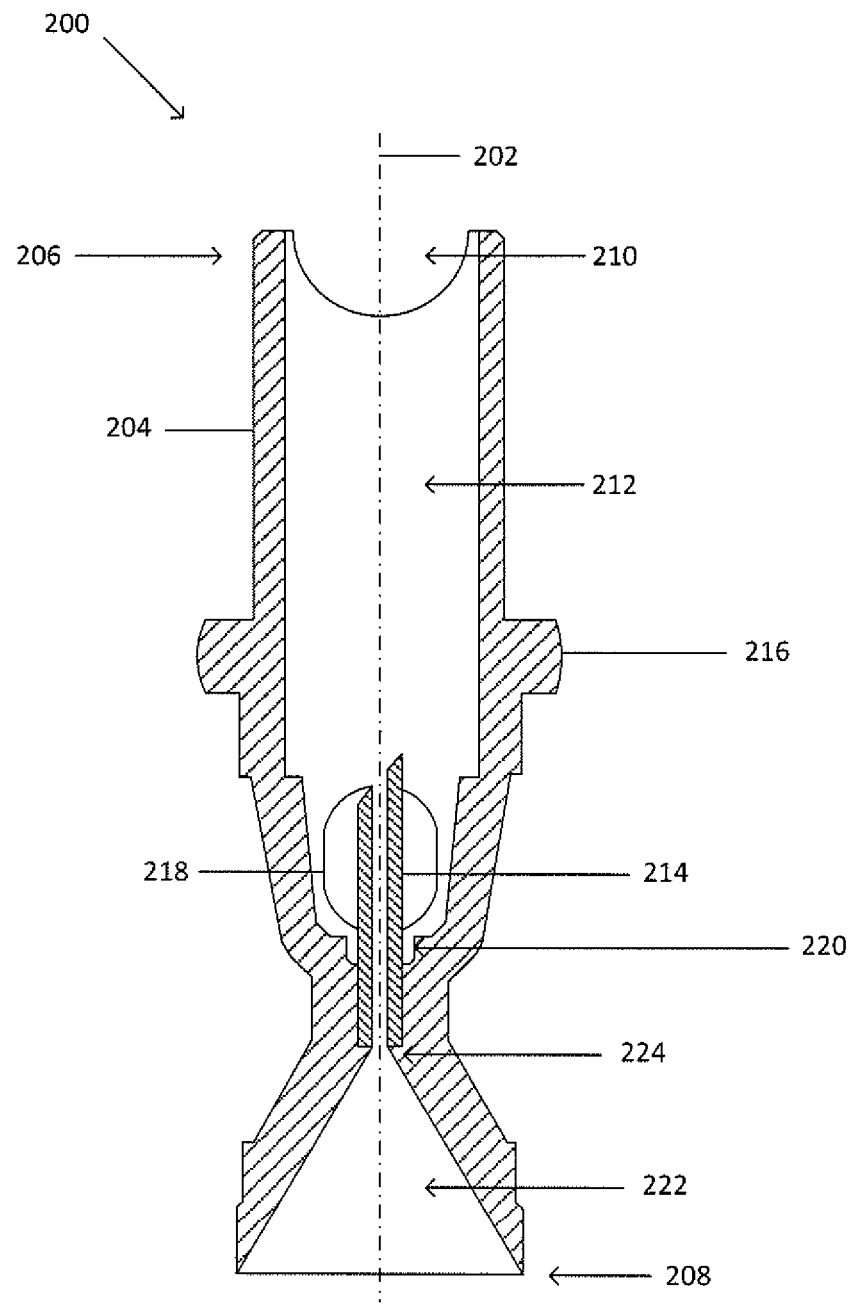

FIG. 2A shows an isometric view of a collector 200. FIG. 2B shows a cross-section view of the collector 200 taken along the line II-II shown in FIG. 2A. Dot-dashed line 202 represents the central or highest-symmetry axis of the collector 200. The collector 200 is similar to the collector 100, except that the collector 200 includes a main body 204 that is more elongated than the main body of the collector 100 in order to accommodate a greater portion of the processing vessel (not shown). The main body 204 includes a first end 206 and a second end 208. A seal may be formed between the second end 208 and an inner wall of the primary vessel to maintain a fluid-tight sealing engagement before, during, and after centrifugation and to inhibit any portion of the suspension flowing between an inner wall of the primary vessel and the main body 204 of the collector 200. The seal may be formed by an interference fit, a grease (such as vacuum grease), an adhesive, an epoxy, by bonding (such as thermal bonding), by welding (such as ultrasonic welding), clamping (such as with a ring or clamp), an insert (such as an O-ring or a collar) that fits between the second end 208 and the inner wall of the primary vessel, or the like.

The first end 206 includes a cavity 212 dimensioned to accept and hold at least a portion of the processing vessel (not shown). The cavity 212 may have a tapered or stepped bottom end 220 on which the processing vessel (not shown) may rest. The first end 206 may also include at least one cut-out 210 to permit proper grip of the processing vessel (not shown) for insertion and removal. The collector 200 funnels the target material from the suspension into an internal concave opening 222 at the second end 208, through a cannula 214, and into a processing vessel (not shown) located within the cavity 212. The cannula 214 may rest on a shelf 224 so that an inner bore of the cannula 214 sits flush with an inner wall of the concave opening 222, as shown in FIG. 2B.

The collector 200 may include a shoulder 216, which extends circumferentially around the main body 204. The shoulder 216 may be larger than the inner diameter of the primary vessel so as to rest on the open end of the primary vessel and, upon applying a lock ring (not shown) to the outside of the primary vessel and the shoulder 216, to inhibit movement of the collector 200 relative to the primary vessel. The lock ring (not shown) applies pressure to the primary vessel along the shoulder 216. The lock ring may be a two-piece ring, a one piece ring wrapping around the full circumference of the primary vessel, or a one piece ring wrapping around less than the full circumference of the primary vessel, such as one-half (½), five-eighths (⅝), two-thirds (⅔), three-quarters (¾), seven-eighths (⅞), or the like. Alternatively, the shoulder 216 may fit within the primary vessel. Alternatively, the shoulder 216 may be a clip, such that the shoulder 216 may include a catch into which the primary vessel may be inserted to inhibit movement of the collector 200 relative to the primary vessel. Alternatively, the shoulder 216 may form an interference fit with the inner wall of the primary vessel around which a seal ring may be placed.

As shown in FIG. 2A, the collector 200 may include at least one window 218 to access the cavity 212 through an inner wall of the main body 204. The at least one window 218 permits an operator to confirm proper placement of the processing vessel (not shown) within the cavity 212. The at least one window 218 also allows fluid discharged from the cannula 214 to flow out of the collector 200 and into a space formed between the collector 200 and the primary vessel (not shown) and above the seal between the second end 208 and the inner wall of the primary vessel.

Figure 2C:
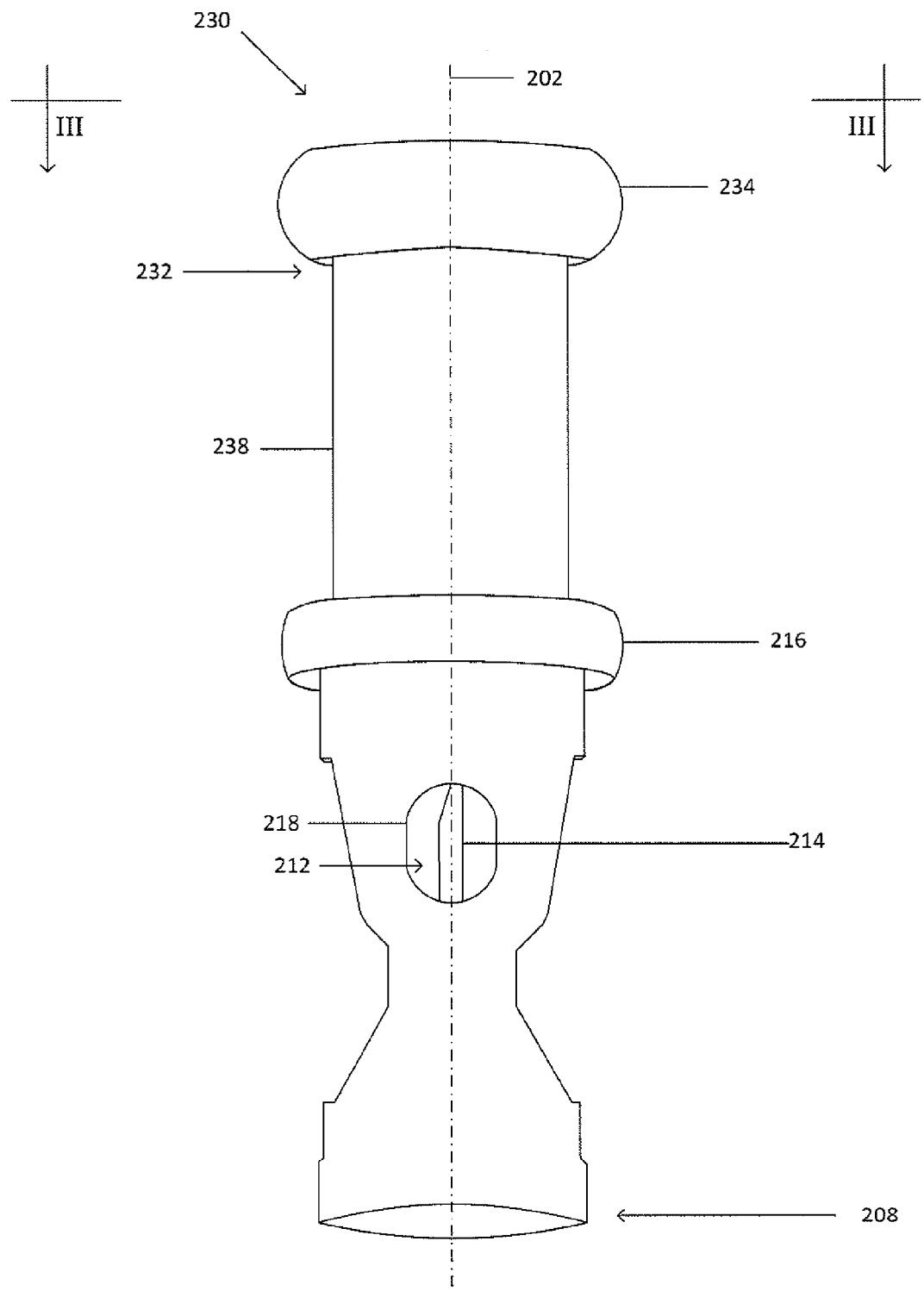
FIGS. 2C-2D show an example collector.
Figure 2D:
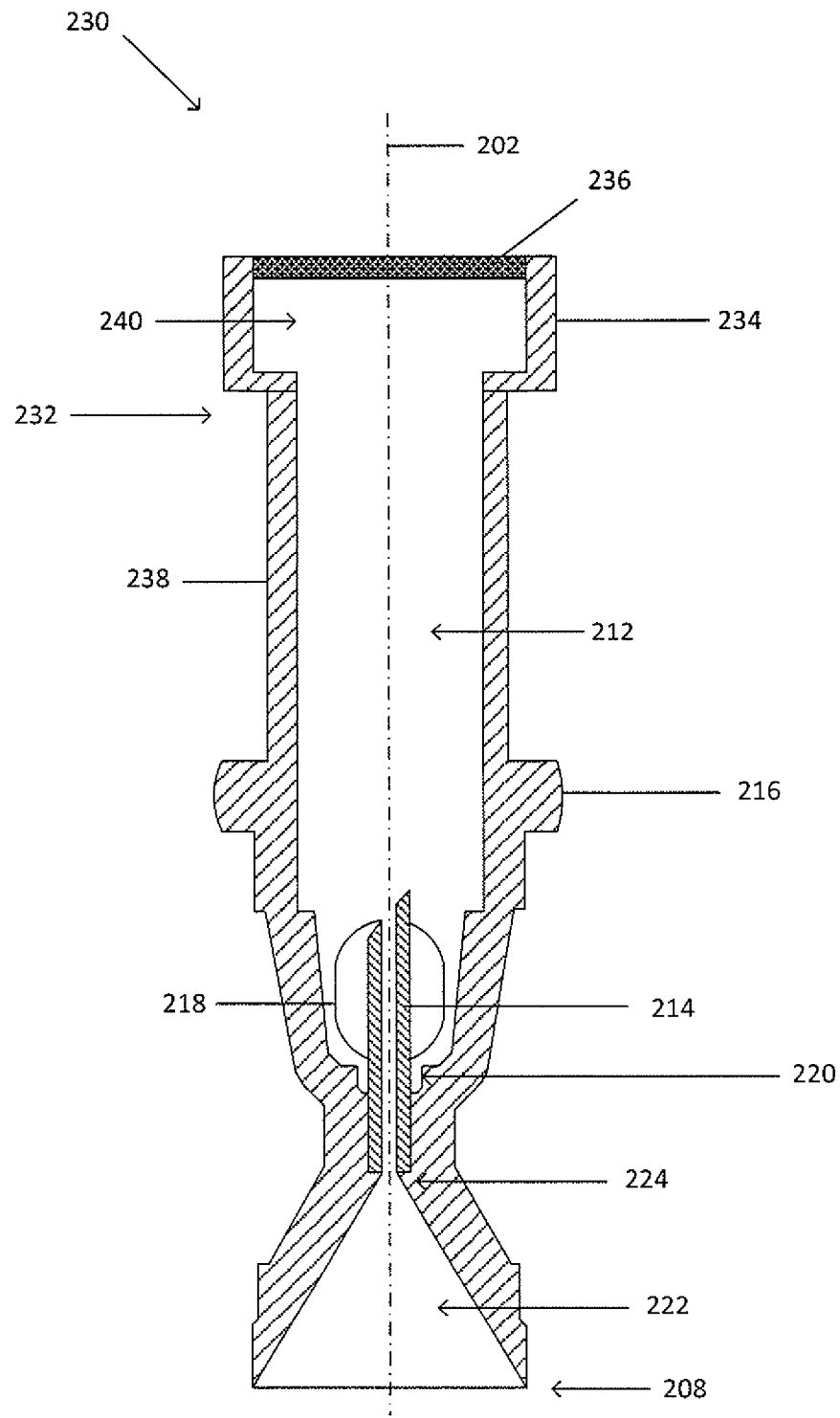

FIG. 2C shows an isometric view of a collector 230. FIG. 2D shows a cross-section view of the collector 230 taken along the line III-III shown in FIG. 2C. The collector 230 is similar to the collector 200, except that the collector 230 includes a main body 238 including an extension 234 extending away from a first end 232 and a lid 236 to at least temporarily seal an opening 240 within the extension 234. The opening 240 may be in fluid communication with the cavity 212 at the first end 232. The lid 236 may removable, puncturable and resealable (e.g. a flap lid), or puncturable and non-resealable (e.g. a foil lid). The extension 234 may be sized to accept the lid 236 when punctured such that a portion of the lid 236 does not extend into the cavity 212 at the first end 232. Note that the collector 230 does not include the at least one cut-out 210.

The main body can be composed of a variety of different materials including, but not limited to, a ceramic; metals; organic or inorganic materials; and plastic materials, such as polyoxymethylene ("Delrin®"), polystyrene, acrylonitrile butadiene styrene ("ABS") copolymers, aromatic polycarbonates, aromatic polyesters, carboxymethylcellulose, ethyl cellulose, ethylene vinyl acetate copolymers, nylon, polyacetals, polyacetates, polyacrylonitrile and other nitrile resins, polyacrylonitrile-vinyl chloride copolymer, polyamides, aromatic polyamides ("aramids"), polyamide-imide, polyarylates, polyarylene oxides, polyarylene sulfides, polyarylsulfones, polybenzimidazole, polybutylene terephthalate, polycarbonates, polyester, polyester imides, polyether sulfones, polyetherimides, polyetherketones, polyetheretherketones, polyethylene terephthalate, polyimides, polymethacrylate, polyolefins (e.g., polyethylene, polypropylene), polyallomers, polyoxadiazole, polyparaxylene, polyphenylene oxides (PPO), modified PPOs, polystyrene, polysulfone, fluorine containing polymer such as polytetrafluoroethylene, polyurethane, polyvinyl acetate, polyvinyl alcohol, polyvinyl halides such as polyvinyl chloride, polyvinyl chloride-vinyl acetate copolymer, polyvinyl pyrrolidone, polyvinylidene chloride, specialty polymers, polystyrene, polycarbonate, polypropylene, acrylonitrite butadiene-styrene copolymer, butyl rubber, ethylene propylene diene monomer; and combinations thereof.

The cannula can be composed of a variety of different materials including, but not limited to, a ceramic; metals; organic or inorganic materials; and plastic materials, such as a polypropylene, acrylic, polycarbonate, or the like; and combinations thereof. The cannula may have a tip along a longitudinal axis of the cannula.

Collector-Processing Vessel System

Figure 3B:
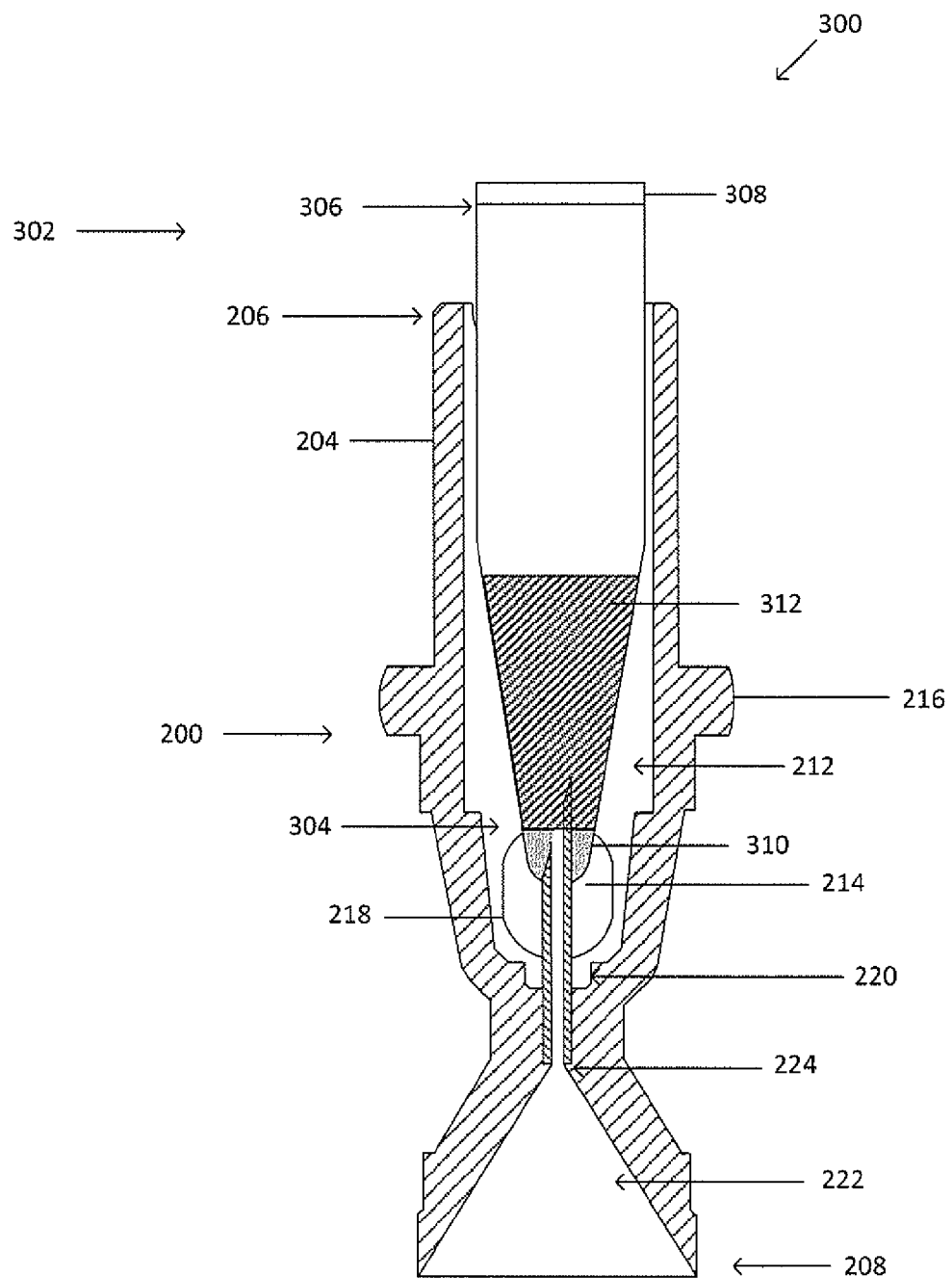

FIG. 3A shows an exploded view of the example collector 200 and processing vessel 302. FIG. 3B shows a cross-sectional view of the processing vessel 302 inserted into the cavity 212 at the first end 206 of the collector 200 taken along the line IV-IV shown in FIG. 3A. The collector 200 and processing vessel 302 form a collector-processing vessel system 300. The processing vessel 302 may be an Eppendorf tube, a syringe, or a test tube and has a closed end 304 and an open end 306. The open end 306 is sized to receive a cap 308. The cap 308 may be composed of re-sealable rubber or other suitable re-sealable material that can be repeatedly punctured with a needle or other sharp implement to access the contents stored in the processing vessel 302 interior and re-seals when the needle or implement is removed. Alternatively, the processing vessel 302 may also have two open ends that are sized to receive caps. The processing vessel 302 may have a tapered geometry that widens or narrows toward the open end 306; the processing vessel 302 may have a generally cylindrical geometry; or, the processing vessel 302 may have a generally cylindrical geometry in a first segment and a cone-shaped geometry in a second segment, where the first and second segments are connected and continuous with each other. Although at least one segment of the processing vessel 302 has a circular cross-section, in other embodiments, the at least one segment can have elliptical, square, triangular, rectangular, octagonal, or any other suitable cross-sectional shape. The processing vessel 302 can be composed of a transparent, semitransparent, opaque, or translucent material, such as plastic or another suitable material. The processing vessel includes a central axis 314, which when inserted into the cavity 212 is coaxial with the central axis 202 of the collector 200. The processing vessel 302 may also include a plug 310 at the closed end 304 to permit the introduction of the target material or to exchange the target material with a displacement fluid 312. The closed end 304 may be threaded to provide for a threaded connection with a threaded cavity 212 of the collector 200. The processing vessel 302 may be composed of glass, plastic, or other suitable material.

The plug 310 may be composed of re-sealable rubber or other suitable re-sealable material that can be repeatedly punctured with a needle or other sharp implement to access the contents of the processing vessel 302 interior or permit introduction of contents into the processing vessel 302 and re-seals when the needle or implement is removed. The plug 310 may be inserted into the processing vessel 302 such that a seal is maintained between the plug 310 and the processing vessel 302, such as by an interference fit. Alternatively, the plug 310 can be formed in the closed end 304 of the processing vessel 302 using heated liquid rubber that can be shaped while warm or hot and hardens as the rubber cools. An adhesive may be used to attach a plug 310 to the inner wall of the processing vessel can be a polymer-based adhesive, an epoxy, a contact adhesive or any other suitable material for bonding or creating a thermal bond. Alternatively, the plug 310 may be injected into the processing vessel 302. Alternatively, the plug 310 may be thermally bonded to the processing vessel 302.

In the example of FIG. 3B, the cannula 214 has a tapered tip that punctures the plug 310 and extends into an inner cavity of the processing vessel 302 with the shaft of the cannula 214 not extending into the inner cavity of the processing vessel 302. As explained in greater detail below, the inner cavity of the processing vessel 302 holds the target material. The cannula 214 may be covered by a resealable sleeve (not shown) to prevent the target material from flowing out unless the processing vessel 302 is in the cavity 212 to a depth that allows the cannula 214 to just penetrate the processing vessel 302. The resealable sleeve (not shown) covers the cannula 214, is spring-resilient, can be penetrated by the cannula 214, and is made of an elastomeric material capable of withstanding repeated punctures while still maintaining a seal.

As shown in FIGS. 3A-3B, the processing vessel 302 may be loaded with a displacement fluid 312 prior to insertion into the collector 200. The displacement fluid 312 displaces the target material, such that when the collector 200 and processing vessel 302 are inserted into the primary vessel (not shown) including the target material, and the collector, processing vessel, and primary vessel undergo centrifugation, the displacement fluid 312 flows out of the processing vessel 302 and into the primary vessel, and, through displacement, such as through buoyant displacement (i.e. lifting a material upwards), pushes the target material through the cannula 214 and into the processing vessel 302.

The displacement fluid 312 has a greater density than the density of the desired target material of the suspension (the density may be greater than the density of a subset of suspension fractions or all of the suspension fractions) and is inert with respect to the suspension materials. For example, the displacement fluid may have a density that is approximately 0.0001 to approximately 0.1 g/cm$^3$ greater than the density of the desired target material. The displacement fluid 312 may be miscible or immiscible in the suspension fluid. Examples of suitable displacement fluids include, but are not limited to, solution of colloidal silica particles coated with polyvinylpyrrolidone (e.g. Percoll), polysaccharide solution (e.g. Ficoll), iodixanol (e.g. OptiPrep), an organic solvent, a liquid wax, an oil, a gas, and combinations thereof; olive oil, mineral oil, silicone oil, immersion oil, mineral oil, paraffin oil, silicon oil, fluorosilicone, perfluorodecalin, perfluoroperhydrophenanthrene, perfluorooctylbromide, and combinations thereof; organic solvents such as 1,4-Dioxane, acetonitrile, ethyl acetate, tert-butanol, cyclohexanone, methylene chloride, tert-Amyl alcohol, Cert-Butyl methyl ether, butyl acetate, hexanol, nitrobenzene, toluene, octanol, octane, propylene carbonate, tetramethylene sulfones, and ionic liquids; polymer-based solutions; surfactants; perfluoroketones, such as perfluorocyclopentanone and perfluorocyclohexanone, fluorinated ketones, hydrofluoroethers, hydrofluorocarbons, perfluorocarbons, perfluoropolyethers, silicon and silicon-based liquids, such as phenylmethyl siloxane; and combinations thereof.

The processing vessel 302 may also include a processing solution (not shown) to effect a transformation on the target material when the target material enters the processing vessel 302. The processing solution (not shown) may be a preservative, a cell adhesion solution, a dye, or the like. Unlike the displacement fluid 312, most, if not all, of the processing solution (not shown) remains within the processing vessel 302 upon centrifugation, thereby effecting the transformation on the target material in one manner or another (i.e. preserving, increasing adhesion properties, or the like). The processing solution (not shown) may be introduced as a liquid or as a liquid contained in a casing. The casing may be dissolvable in an aqueous solution but not in the displacement fluid 312

(such as gel cap); or, the casing may be breakable, such that the casing breaks when the processing vessel 302 is shaken in a vortex mixer. Additionally, more than one processing solution may be used.

The processing vessel 302 may include a flexible cap that can be pushed to dispense a pre-determined volume therefrom and onto a substrate, such as a slide or a well plate. The cap 308 may be flexible or the cap 308 may be removed and the flexible cap inserted into the open end 306. Alternatively, the processing vessel 302 may be attached to (i.e. after accumulating the target material) or may include a dispenser, which is capable of dispensing a pre-determined volume of target material from the processing vessel 302 onto another substrate, such as a microscope slide. The dispenser may repeatedly puncture the re-sealable cap 308 or compress the material within the processing vessel 302 to withdraw and dispense the pre-determined volume of target material onto the substrate. Alternatively, the cap 308 may be removed and the dispenser (not shown) may be inserted directly into the processing vessel 302 to dispense the buffy coat-processing solution mixture.

Collector-Canopy System

Figure 4A:
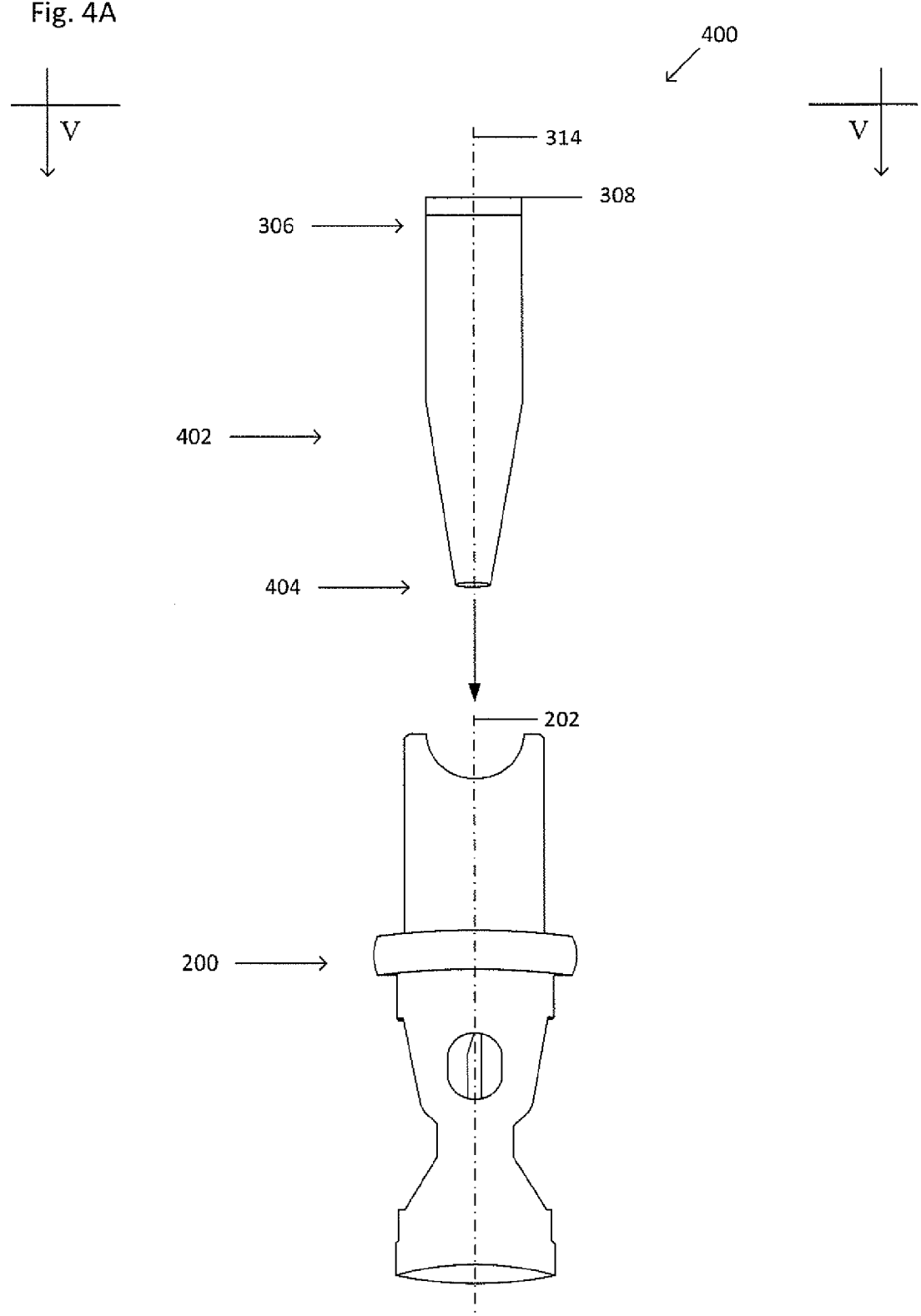
FIGS. 4A-4B show an example collector-canopy system.
Figure 4B:
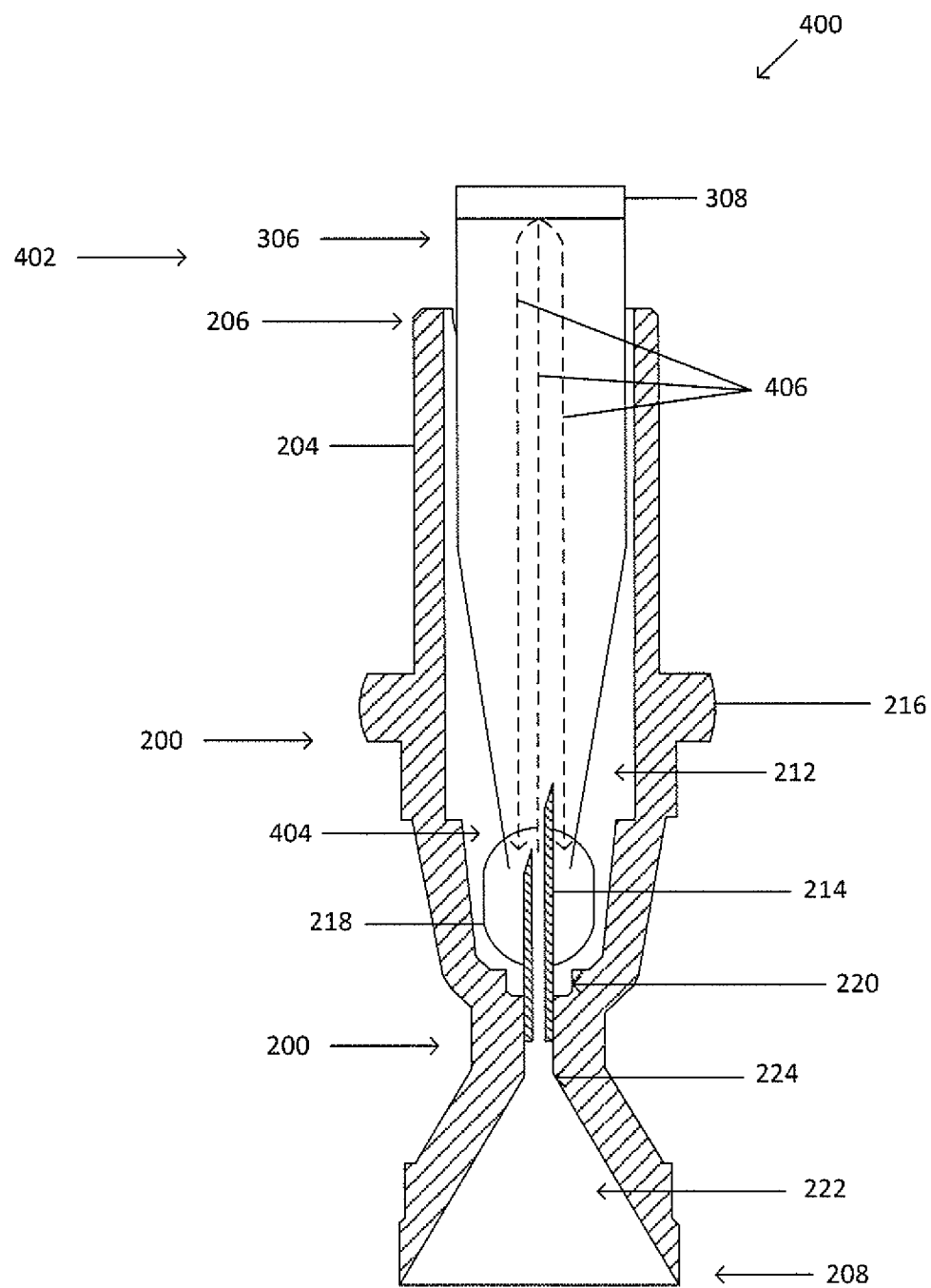

FIG. 4A shows an exploded view of the example collector 200 and a canopy 402. FIG. 4B shows a cross-sectional view of the canopy 402 inserted into the cavity 212 of the collector 200 taken along the line V-V shown in FIG. 4A. The collector 200 and canopy 402 form a collector-canopy system 400. The canopy 402 is similar to the processing vessel 302, except that the canopy has a second open end 404. When the collector-canopy system 400 is inserted into the primary vessel, some fluid within the primary vessel, such as a portion of the suspension, a portion of a suspension fraction, a portion of a clearing fluid, or the like, may be discharged through the cannula 214. The canopy 402 inhibits a portion of the fluid in the primary vessel that may be discharged through the cannula 214 from escaping from the opening of the first end 206 of the collector 200. The discharged fluid, having been blocked by the canopy 402, flows out of the second open end 404, and out of the window 218. Dashed lines 406 show fluid flow as the fluid is discharged through the cannula 214 and retained by the canopy 402.

Alternatively, when the collector 230 is used, the lid 236 of the collector 230 inhibits a portion of the fluid in the primary vessel that may be discharged through the cannula 214 from escaping from the opening of the first end 206 of the collector 200 in a manner similar to that of the canopy 402.

Sealing Ring

Figure 5A:
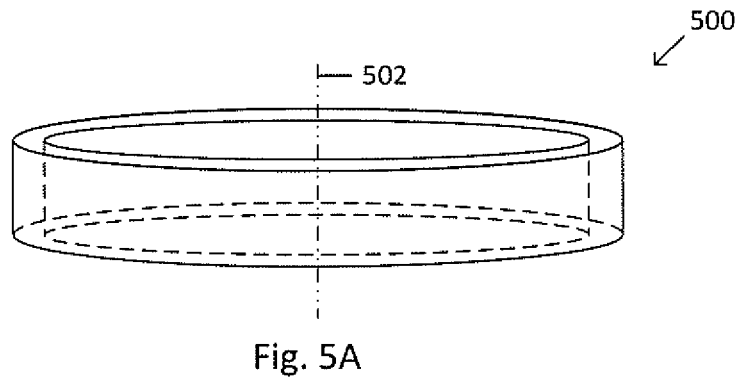
FIGS. 5A-5B show an example sealing ring.
Figure 5B:
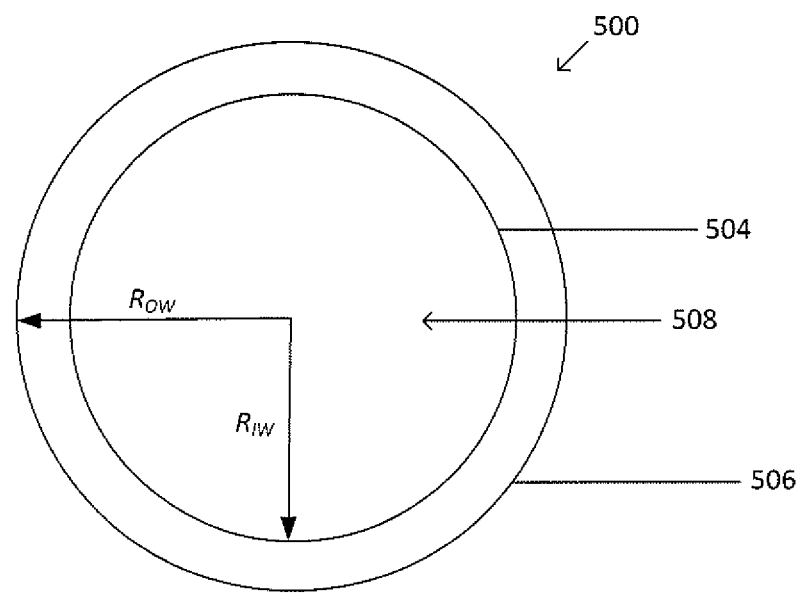

FIG. 5A shows an isometric view of a sealing ring 500. FIG. 5B shows a top down view of the sealing ring 500. Dot-dashed line 502 represents the central or highest-symmetry axis of the sealing ring 500. The sealing ring 500 includes an inner wall 504, an outer wall 506, and a cavity 508. In FIG. 5B, $R_{IW}$ represents the radial distance from the center of the sealing ring 500 to the inner wall 504, and $R_{OW}$ represents the radial distance from the center of the sealing ring 500 to the outer wall 506. The sealing ring 500 is configured to fit around a primary vessel, such as a tube. The cavity 508 is sized and shaped to receive the primary vessel. The sealing ring 500 may be tightened, such that the size of the cavity 508 and the radii of the inner and outer walls 504 and 506 are reduced by circumferentially applying an approximately uniform, radial force, such as the radial force created by a clamp, around the outer wall 506 directed to the central axis 502 of the sealing ring 500. When the sealing ring 500 is tightened around the primary vessel, the uniform force applied to the sealing ring 500 is applied to the primary vessel, thereby causing the primary vessel to constrict. When the radial force is removed from the sealing ring 500, the sealing ring 500 remains tightened and in tension around the primary vessel.

Figure 5C:
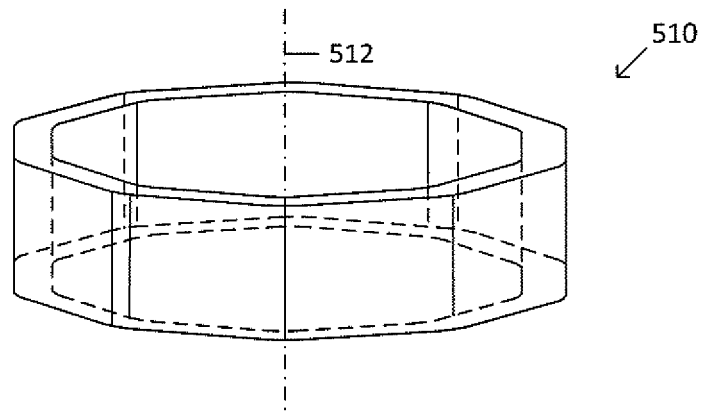
FIGS. 5C-5D show an example sealing ring.
Figure 5D:
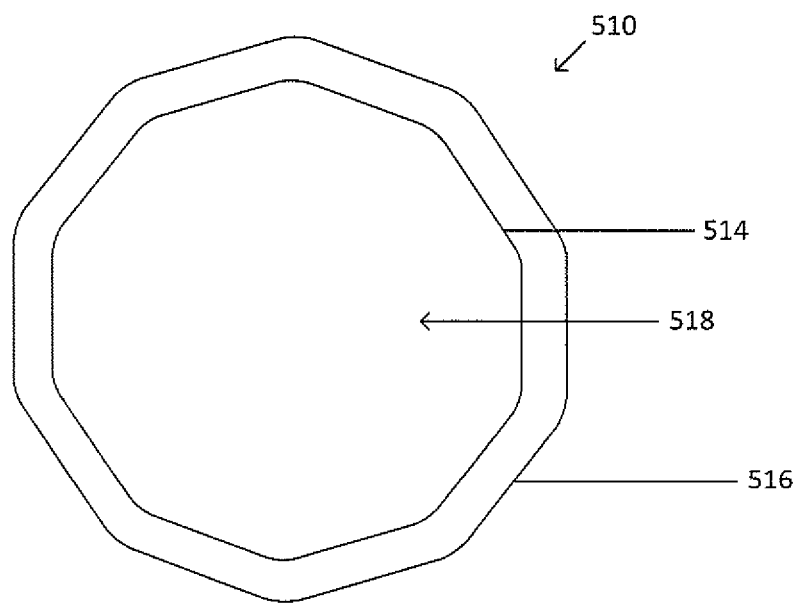

The sealing ring may be any shape, including, but not limited to, circular, triangular, or polyhedral. FIG. 5C shows an isometric view of a sealing ring 510. FIG. 5D shows a top down view of the sealing ring 510. Sealing ring 510 is similar to sealing ring 500, except sealing ring 510 is polyhedral. Dot-dashed line 512 represents the central or highest-symmetry axis of the sealing ring 510. The sealing ring 510 includes an inner wall 514, an outer wall 516, and a cavity 518. The sealing ring may be composed of a metal, such as brass, a polymer, or combinations thereof.

Figure 5E:
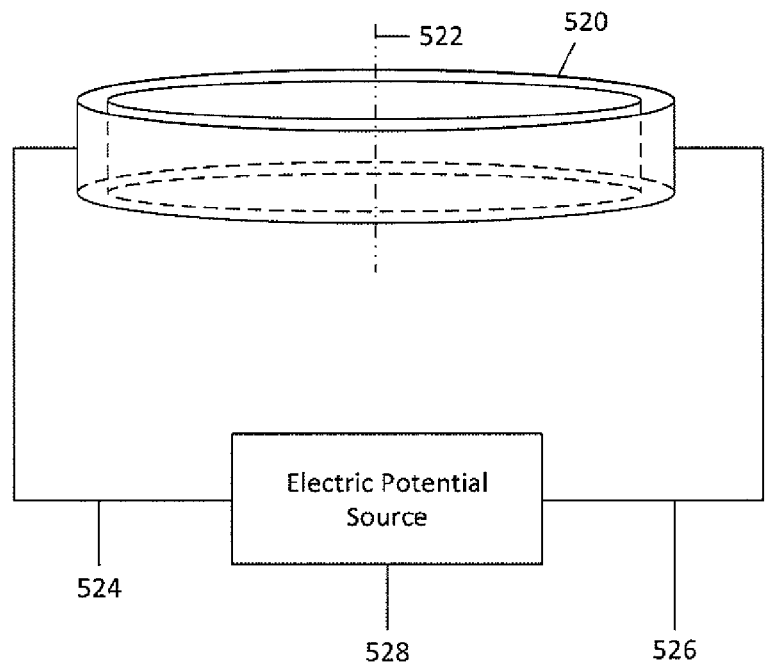
FIGS. 5E-5F show an example sealing ring.
Figure 5F:
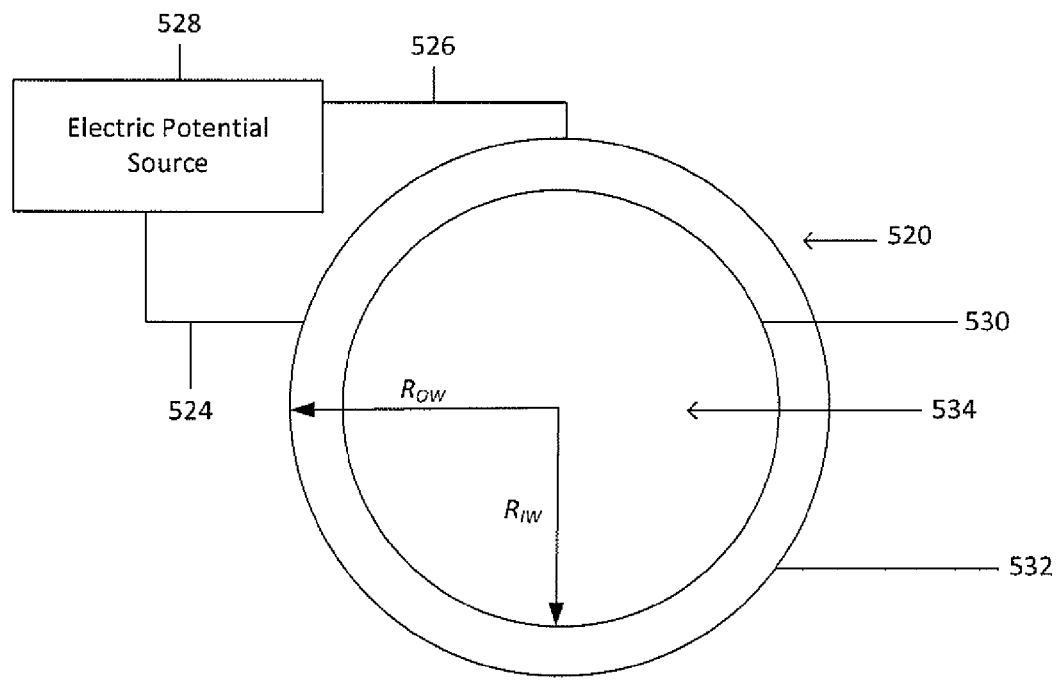

Alternatively, as shown in FIG. 5E, a sealing ring 520 may be composed of a piezoelectric material. FIG. 5F shows a top down view of the sealing ring 520. Dot-dashed line 522 represents the central or highest-symmetry axis of the sealing ring 520. The sealing ring 520 may be connected to an electric potential source 528, such as a battery, via a first lead 524 and a second lead 526. The electric potential source 528 creates a mechanical strain that causes the sealing ring 520 to tighten (i.e. sealing ring 520 radii decrease). The sealing ring 520 includes an inner wall 530, an outer wall 532, and a cavity 534. In FIG. 5F, $R_{IW}$ represents the radial distance from the center of the sealing ring 520 to the inner wall 530, and $R_{OW}$ represents the radial distance from the center of the sealing ring 520 to the outer wall 532. Alternatively, the sealing ring 520 may be in a naturally tightened stated. When applying the electric potential the sealing ring 520 expands. Alternatively, a portion of the sealing ring may be composed of the piezoelectric material, such that the piezoelectric portion acts as an actuator to cause the other portion of the sealing ring to tighten and apply the substantially uniform circumferential pressure on the primary vessel, thereby constricting the primary vessel to form the seal.

Figure 5G:
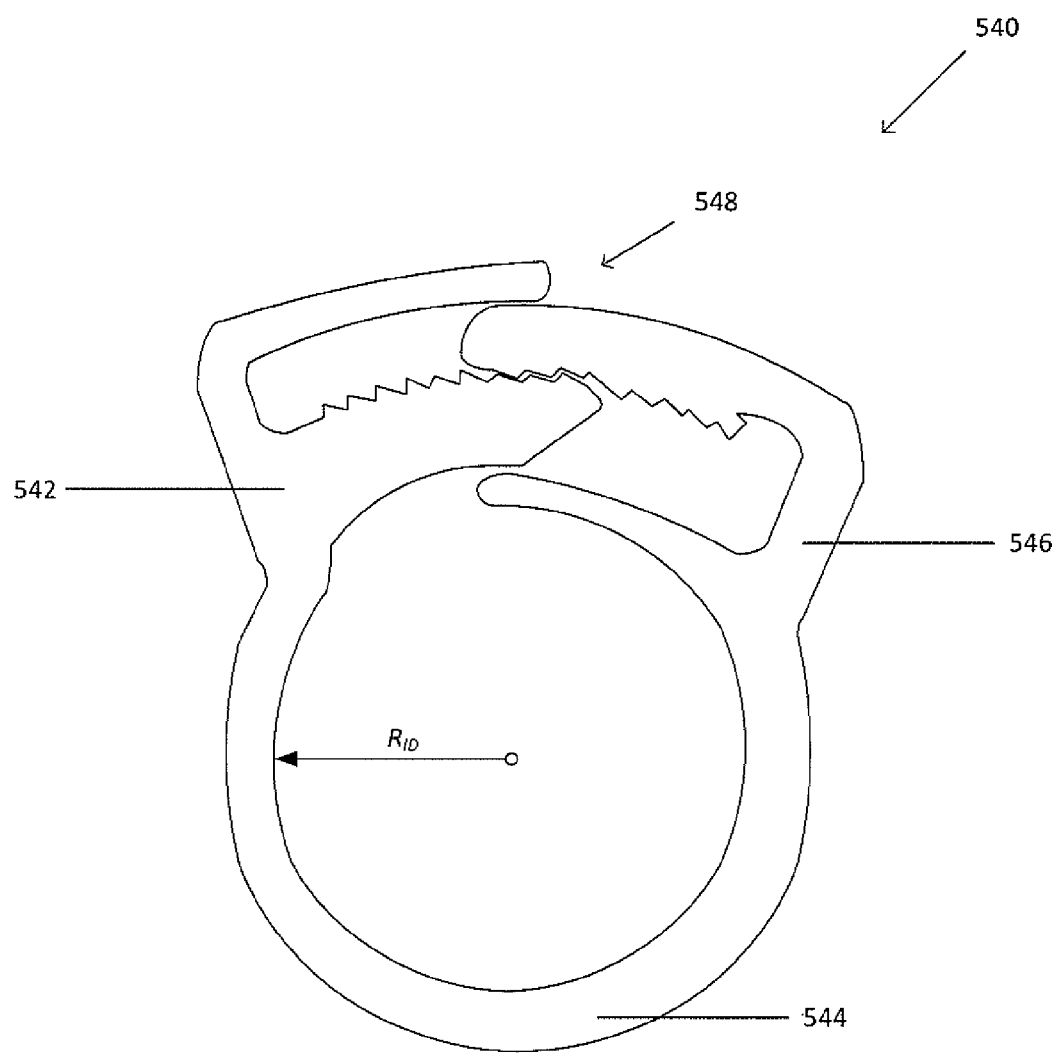
FIG. 5G shows an example sealing ring.

FIG. 5G shows an isometric view of a sealing ring 540. The sealing ring includes an adjustment mechanism 548 to adjust the inner diameter $R_{ID}$. The collapsible ring includes a first end 542 and a second end 546, the first and second ends 542 and 546 being joined by a band portion 544. The first and second ends 542 and 546 include complementary portions of the adjustment mechanism 548. The adjustment mechanism 548 includes, but is not limited to, a ratchet, tongue and groove, detents, or the like.

The sealing ring may also include a thermal element, such as a heated wire. The thermal element may soften the primary vessel for constriction. Alternatively, the thermal element may melt the primary vessel to provide a more adherent seal. Alternatively, the thermal element may cause the sealing ring to compress, thereby forming a seal between the primary vessel and float.

Sequential Density Fractionation Method

Sequential density fractionation is the division of a sample into fractions or of a fraction of a sample into sub-fractions by a step-wise or sequential process, such that each step or sequence results in the collection or separation of a different fraction or sub-fraction from the preceding and successive steps or sequences. In other words, sequential density fractionation provides individual sub-populations of a population or individual sub-sub-populations of a sub-population of a population through a series of steps. For example, buffy coat is a fraction of a whole blood sample. The buffy coat fraction can be further broken down into sub-fractions including, but not limited to, reticulocytes, granulocytes, lymphocytes/monocytes, and platelets. These sub-fractions may be obtained individually by performing sequential density fractionation.

For the sake of convenience, the methods are described with reference to an example suspension of anticoagulated whole blood. But the methods described below are not intended to be so limited in their scope of application. The methods, in practice, can be used with any kind of suspension. For example, a sample suspension can be urine, blood, bone marrow, cystic fluid, ascites fluid, stool, semen, cerebrospinal fluid, nipple aspirate fluid, saliva, amniotic fluid, vaginal secretions, mucus membrane secretions, aqueous humor, vitreous humor, vomit, and any other physiological fluid or semi-solid. It should also be understood that a target material can be a fraction of a sample suspension, such as buffy coat, a cell, such as ova, fetal material (such as trophoblasts, nucleated red blood cells, fetal red blood cells, fetal white blood cells, fetal DNA, fetal RNA, or the like), or a circulating tumor cell ("CTC"), a circulating endothelial cell, an immune cell (i.e. naïve or memory B cells or naïve or memory T cells), a vesicle, such as an exosome, a liposome, a protein, a nucleic acid, a biological molecule, a naturally occurring or artificially prepared microscopic unit having an enclosed membrane, parasites (e.g. spirochetes, such as *Borrelia burgdorferi* which cause Lyme disease; malaria-inducing agents), microorganisms, viruses, or inflammatory cells. Additionally, the fetal material may be any biological material that is present in a pregnant female as a result of the pregnancy. Alternatively, the sample may be a biological solid, such as tissue, that has been broken down, such as by collagenase, prior to or after being added to the primary vessel.

For example, target material enrichment is a process by which the target materials are purified relative to non-target material. For example, the target material may be enriched relative to non-target material, thereby having a ratio as low as 1 part target material, such as a single cell, protein, DNA, or the like, to 30,000,000 parts non-target material. Other ratios may include, but at not limited to, as low as approximately 1:25,000,000, 1:15,000,000, 1:10,000,000, 1:5,000,000, 1:1,000,000, 1:250,000, 1:100,000, 1:50,000, 1:25,000, 1:10,000, 1:1,000, 1:100, 1:10, or 1:1.

Figure 6:
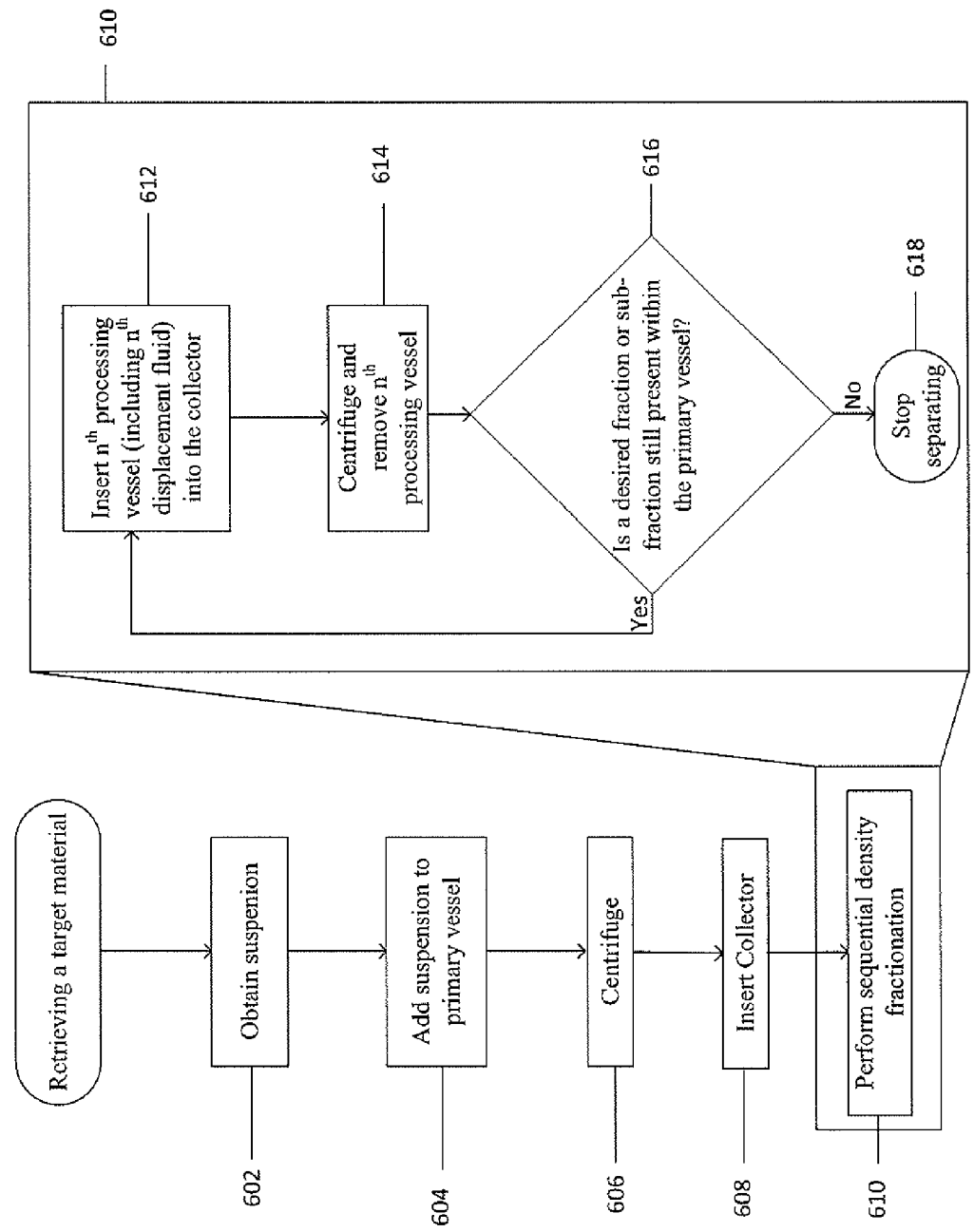
FIG. 6 shows a flow diagram of an example method for retrieving a target material.

FIG. 6 shows a flow diagram for an example method for retrieving target material. In block 602, a suspension, such as anticoagulated whole blood, is obtained. In block 604, the whole blood is added to a primary vessel, such as a test tube. A float may also be added to the primary vessel. For the sake of convenience, the methods are described with reference to the float, but the methods described below are not intended to be so limited in their application and may be performed without the float.

Figure 7:
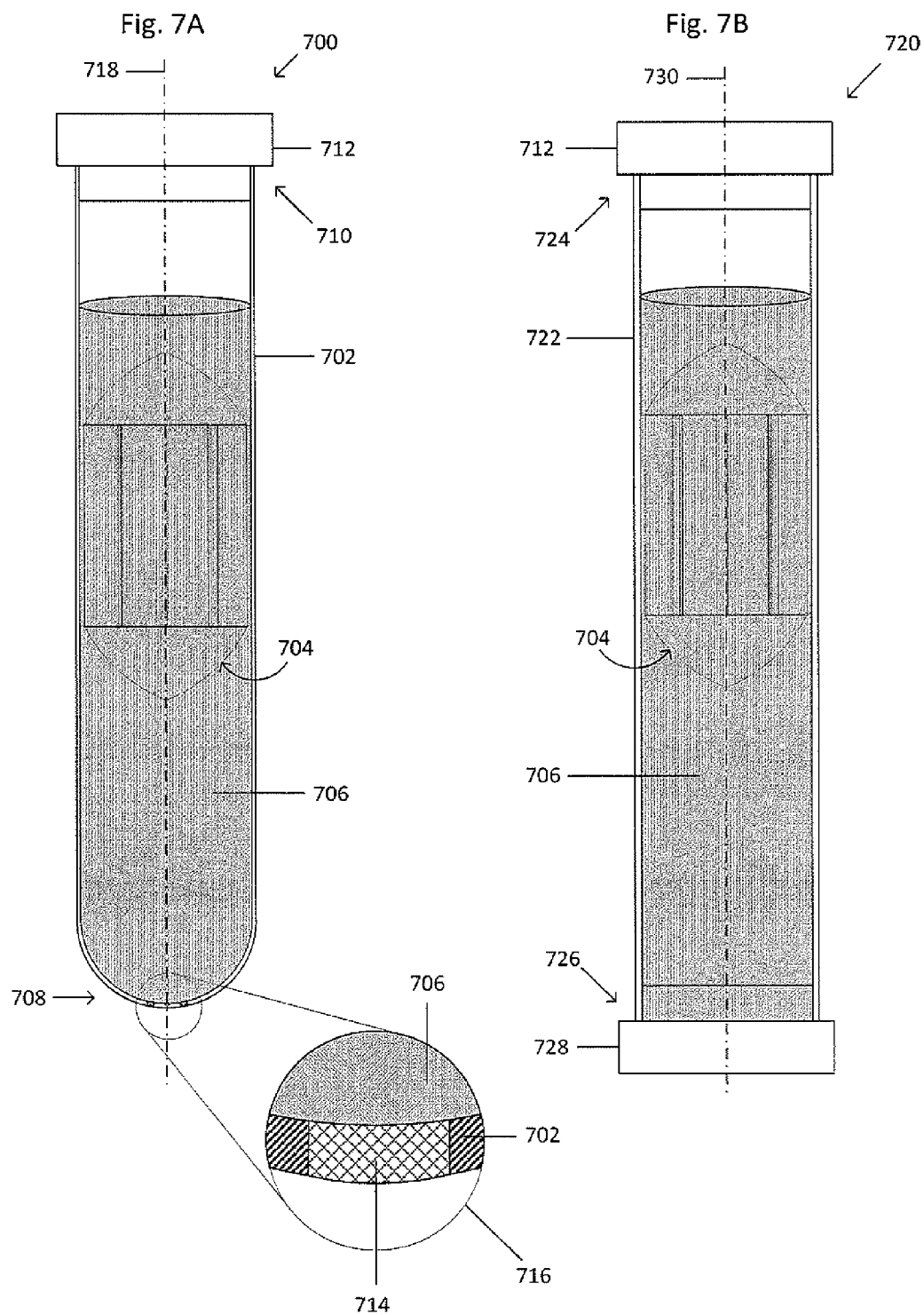
FIGS. 7A-7B show example float and primary vessel systems.

FIG. 7A shows an isometric view of an example primary vessel and float system 700. The system 700 includes a primary vessel 702 and a float 704 suspended within whole blood 706. In the example of FIG. 7A, the primary vessel 702 has a circular cross-section, a first open end 710, and a second closed end 708. The open end 710 is sized to receive a cap 712. The primary vessel may also have two open ends that are sized to receive caps, such as the example tube and separable float system 720 shown FIG. 7B. The system 720 is similar to the system 700 except the primary vessel 702 is replaced by a primary vessel 722 that includes two open ends 724 and 726 configured to receive the cap 712 and a cap 728, respectively. The primary vessels 702 and 722 have a generally cylindrical geometry, but may also have a tapered geometry that widens, narrows, or a combination thereof toward the open ends 710 and 724, respectively. Although the primary vessels 702 and 722 have a circular cross-section, in other embodiments, the primary vessels 702 and 722 can have elliptical, square, triangular, rectangular, octagonal, or any other suitable cross-sectional shape that substantially extends the length of the tube. The primary vessels 702 and 722 can be composed of a transparent, semitransparent, opaque, or translucent material, such as plastic or another suitable material. The primary vessels 702 and 722 each include a central axis 718 and 730, respectively. The primary vessel 702 may also include a septum 714, as seen in magnified view 716, at the closed end 708 to permit the removal of a fluid, the suspension, or a suspension fraction, whether with a syringe, a pump, by draining, or the like. The primary vessel 702 may have an inner wall and a first diameter.

The septum 714 may be composed of re-sealable rubber or other suitable re-sealable material that can be repeatedly punctured with a needle or other sharp implement to access the contents of the primary vessel 702 interior and re-seals when the needle or implement is removed. The septum 714 may be inserted into the primary vessel 702 such that a seal is maintained between the septum 714 and the primary vessel 702, such as by an interference fit. Alternatively, the septum 714 can be formed in the openings and/or the bottom interior of the tube using heated liquid rubber that can be shaped while warm or hot and hardens as the rubber cools. An adhesive may be used to attach the septum 714 to the wall of the opening and tube interior and can be a polymer-based adhesive, an epoxy, a contact adhesive or any other suitable material for bonding rubber to plastic or creating a thermal bond. Alternatively, the septum 714 may be thermally bonded to the primary vessel 702.

The float 704 includes a main body, two teardrop-shaped end caps, and support members radially spaced and axially oriented on the main body. Alternatively, the float 704 may not include any support members. Alternatively, the float 704 may include support members which do not engage the inner wall of the primary vessel 702.

In alternative embodiments, the number of support members, support member spacing, and support member thickness can each be independently varied. The support members can also be broken or segmented. The main body is sized to have an outer diameter that is less than the inner diameter of the primary vessel 702, thereby defining fluid retention channels between the outer surface of the main body and the inner wall of the primary vessel 702. The surfaces of the main body between the support members can be flat, curved or have another suitable geometry. The support members and the main body may be a singular structure or may be separate structures.

Embodiments include other types of geometric shapes for float end caps. The top end cap may be teardrop-shaped, dome-shaped, cone-shaped, or any other appropriate shape. The bottom end cap may be teardrop-shaped, dome-shaped, cone-shaped, or any other appropriate shape. In other embodiments, the main body of the float 704 can include a variety of different support structures for separating samples, supporting the tube wall, or directing the suspension fluid around the float during centrifugation. Embodiments are not intended to be limited to these examples. The main body may include a number of protrusions that provide support for the tube. In alternative embodiments, the number and pattern of protrusions can be varied. The main body may include a single continuous helical structure or shoulder that spirals around the main body creating a helical channel. In other embodiments, the helical shoulder can be rounded or broken or segmented to allow fluid to flow between adjacent turns of the helical shoulder. In various embodiments, the helical shoulder spacing and rib thickness can be independently varied. In another embodiment, the main body may include a support member extending radially from and circumferentially around the main body. In another embodiment, the support members may be tapered.

The float 704 can be composed of a variety of different materials including, but not limited to, metals; organic or inorganic materials; ferrous plastics; sintered metal; machined metal; plastic materials and combinations thereof. The primary vessel 702 may have an inner wall and a first diameter. The float 704 can be captured within the primary vessel 702 by an interference fit, such that under centrifugation, an inner wall of the tube expands to permit axial movement of the float 704. When centrifugation stops, the inner wall reduces back to the first diameter to induce the interference fit. Alternatively, the inner wall may not expand and the interference fit may not occur between the float 704 and the primary vessel 702, such that the float moves freely within the tube before, during, or after centrifugation. The end caps of the float may be manufactured as a portion of the main body, thereby being one singular structure, by machining, injection molding, additive techniques, or the like; or, the end caps may be connected to the main body by a press fit, an adhesive, a screw, any other appropriate method by which to hold at least two pieces together, or combinations thereof.

The cap 712 may be composed of a variety of different materials including, but not limited to, organic or inorganic materials; plastic materials; and combination thereof.

Figure 8:
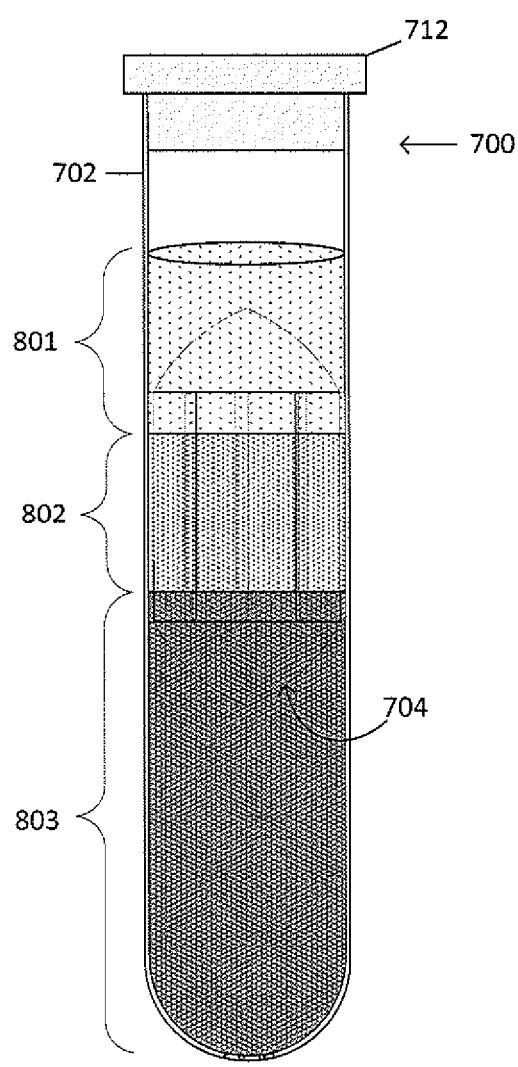
FIG. 8 shows an example float and primary vessel system having undergone density-based separation.

Returning to FIG. 6, in block 606, the primary vessel, the float, and the whole blood undergo density-based separation, such as by centrifugation, thereby permitting separation of the whole blood into density-based fractions along an axial position in the tube based on density. FIG. 8 shows an isometric view of the primary vessel and float system 700 having undergone density-based separation, such as by centrifugation. Suppose, for example, the centrifuged whole blood includes three fractions. For convenience sake, the three fractions include plasma, buffy coat, and red blood cells. However, when another suspension undergoes centrifugation, there may be more than, less than, or the same number of fractions, each fraction having a different density. The suspension undergoes axial separation into three fractions along the length the tube based on density, with red blood cells 803 located on the bottom, plasma 801 located on top, and buffy coat 802 located in between, as shown in FIG. 8. The float 704 may have any appropriate density to settle within one of the fractions. The density of the float 704 can be selected so that the float 704 expands the buffy coat 802 between the main body of the float and the inner wall of the primary vessel. The buffy coat 802 can be trapped within an area between the float 704 and the primary vessel 702.

At least one delineation fluid (not shown) may be used to provide further separation between the target material and any non-target material above and/or below the target material. The at least one delineation fluid (not shown) may have a density greater than or less than the target material. For example, when it is desirous to further separate the buffy coat 802 and the red blood cells 803, the delineation fluid may have a density greater than the buffy coat 802 and less than, the red blood cells 803. The at least one delineation fluid (not shown) may be miscible or immiscible with the suspension fluid and inert with respect to the suspension materials. The at least one delineation fluid (not shown) may also provide an area in which to seal the primary vessel 702, because there is greater delineation and separation between the buffy coat 802 and the red blood cells 803. The at least one delineation fluid (not shown) may be used whether or not a float is used. Examples of suitable delineation fluids include, but are not limited to, solution of colloidal silica particles coated with polyvinylpyrrolidone (e.g. Percoll), polysaccharide solution (e.g. Ficoll), iodixanol (e.g. OptiPrep), cesium chloride, sucrose, sugar-based solutions, polymer-based solutions, surfactants, an organic solvent, a liquid wax, an oil, a gas, and combinations thereof; olive oil, mineral oil, silicone oil, immersion oil, mineral oil, paraffin oil, silicon oil, fluorosilicone, perfluorodecalin, perfluoroperhydrophenanthrene, perfluorooctylbromide, and combinations thereof; organic solvents such as 1,4-Dioxane, acetonitrile, ethyl acetate, tert-butanol, cyclohexanone, methylene chloride, tert-Amyl alcohol, tert-Butyl methyl ether, butyl acetate, hexanol, nitrobenzene, toluene, octanol, octane, propylene carbonate, tetramethylene sulfones, and ionic liquids; polymer-based solutions; surfactants; perfluoroketones, such as perfluorocyclopentanone and perfluorocyclohexanone, fluorinated ketones, hydrofluoroethers, hydrofluorocarbons, perfluorocarbons, perfluoropolyethers, silicon and silicon-based liquids, such as phenylmethyl siloxane; and combinations thereof.

FIG. 9 shows a seal being formed to prevent fluids from moving up or down within the primary vessel. The seal also inhibits float movement. The sealing ring 500 exerts circumferential or radial forces on the primary vessel 702, thereby causing the primary vessel 702 to collapse inwardly against the float 704 magnified view 902 shows the sealing ring 500 tightened around the float and primary vessel system 700. The sealing ring 500, having been placed at an interface of the buffy coat 802 and the red blood cells 803, causes the primary vessel 702 to collapse inwardly until a seal is formed between the primary vessel 702 and the float 704. An outer wall of the sealing ring 500 may sit flush with an outer wall of the primary vessel 702; the outer wall of the sealing ring 500 may extend past the outer wall of the primary vessel 702; or, the outer wall of the primary vessel 702 may extend past the outer wall of the sealing ring 500. The sealing ring 500 remains tightened to maintain the seal, which prevents fluids from moving past the seal in any direction. The sealing ring 500 may also remain in tension. Alternatively, the sealing ring 500 may be overtightened and then the force applied to the sealing ring 500 is removed. The sealing ring 500 may expand slightly, though still remains constricted.

To apply the sealing ring 500 and thereby form the seal, a clamp may be used to circumferentially apply a force directed toward the central axis of the primary vessel 702 to the sealing ring 500 and the float and primary vessel system 700. The sealing ring 500 is placed around the float and primary vessel system 700 after the float and primary vessel system 700 have undergone density-based separation, such as by centrifugation. The sealing ring 500 and float and primary vessel system 700 are then placed into the clamp. The clamp may include a shelf to support the sealing ring 500 against the primary vessel 702. Operation of the clamp may be automated or may be performed manually. Alternatively, the clamp may form a seal between the float 704 and primary vessel 702 without the inclusion of the sealing ring 500. Alternatively, a seal may be formed between the float 704 and the primary vessel 702 such as by ultrasonic welding; or by applying heat or a temperature gradient to deform and/or melt the primary vessel 702 to the float 704. For the sake of convenience, the methods are described with reference to the sealing ring, but the methods described below are not intended to be so limited in their application and may be performed without the sealing ring.

When operation of the clamp is automated, a motor causes translation of either a collet, including collet fingers, or a pressure member to cause compression of the collet fingers. The motor may be connected to the collet or the pressure member by a shaft, such as a cam shaft, and one or more gears. A base engages and holds the object. When the collet is driven by the motor, the pressure member remains stationary. When the pressure member is driven by the motor, the collet remains stationary. The clamp may include a release, so as to cause the pressure member to slide off of the collet fingers 904, thereby removing the clamping force.

Alternatively, the clamp may be, but is not limited to, a collet clamp, an O-ring, a pipe clamp, a hose clamp, a spring clamp, a strap clamp, or a tie, such as a zip tie. The clamp may be used without a sealing ring to provide a seal between a float and a tube.

Figure 10A:
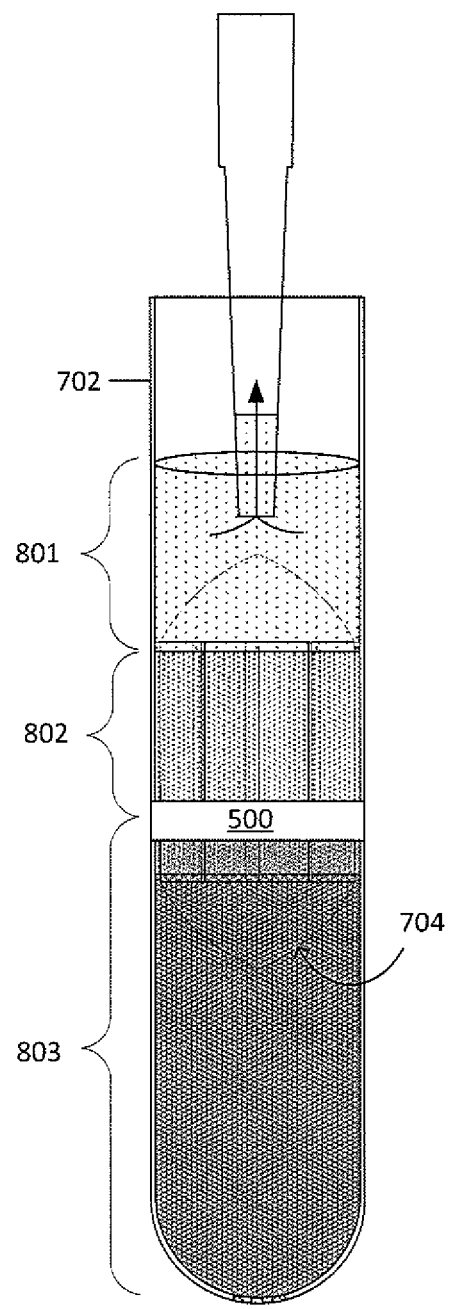
Figure 10C:
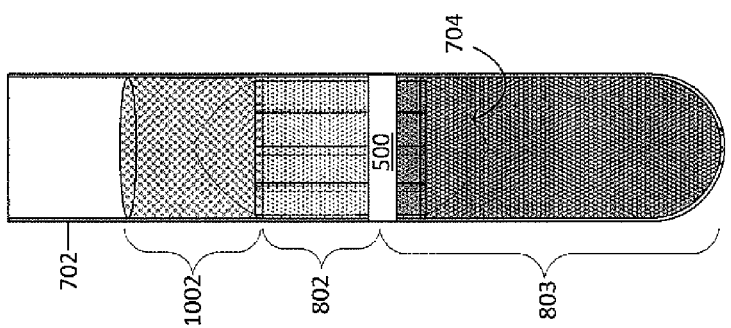
Figure 10B:
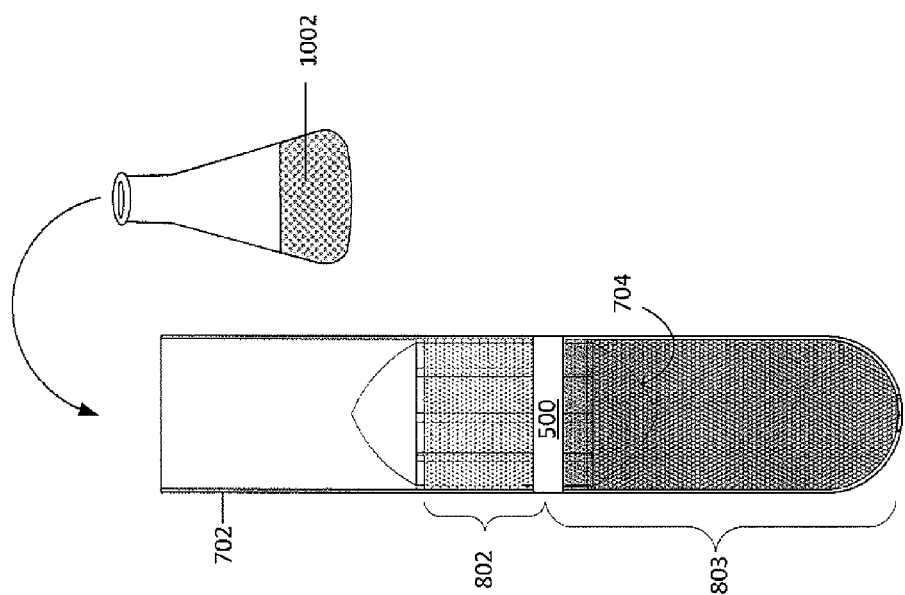

The plasma 801 may be removed from the primary vessel 702, as shown in FIG. 10A, such as by pipetting, suctioning, pouring, or the like. Returning to FIG. 6, in block 608, a clearing fluid may be added to the primary vessel along with a collector-canopy system. FIGS. 10B-10C show a clearing fluid 1002 having a density greater than at least the buffy coat 802 (i.e. may have a density greater than the buffy coat but less than the red blood cells, or may have a density greater than both the buffy coat and the red blood cells, for example) being added to the primary vessel 702. The collector-canopy system 400 may then be added to the primary vessel 702, as shown in FIG. 10D. The second end 208 of the collector 200 forms a seal 1008 with the inner wall of the primary vessel 702 to prevent fluid from flowing around the collector 200 before, during, and after centrifugation. The seal 1008 may be formed between the second end 208 and an inner wall of the primary vessel to maintain a fluid-tight sealing engagement before, during, and after centrifugation and to inhibit any portion of the suspension from being located or flowing between an inner wall of the primary vessel and a main body 204 of the collector 200. The seal may be formed by an interference fit, a grease (such as vacuum grease), an adhesive, an epoxy, thermal bonding, ultrasonic welding, clamping (such as with a ring or clamp), an insert that fits between the second end 208 and the inner wall of the primary vessel, or the like. A lock ring 1004 may be placed over the shoulder 216 of the collector 200 and the open end 710 of the primary vessel 702 to inhibit translation of the collector 200 relative to the primary vessel 702. When the collector-canopy system 400 is inserted, a portion of the clearing fluid 1002 in the primary vessel 702 may be discharged through the cannula 214 and stopped by the canopy 402. The discharged fluid may flow out through the window 218 and into the primary vessel 702, though remaining above the seal between the second end 208 and the inner wall of the primary vessel 702, as seen by the dashed lines 406 in magnified view 1006 which is taken along the line VI-VI.

Returning to FIG. 6, in block 610, sequential density fractionation is performed. Block 610 is also a snapshot of the sequential density fractionation steps. In block 612, an $n^{th}$ processing vessel including an $n^{th}$ displacement fluid is inserted into the collector, such that $n^{th}$ is greater than or equal to first (i.e. second, third, fourth, and so on) as seen in FIG. 10E. Alternatively, the $n^{th}$ displacement fluid may be added to the $n^{th}$ processing vessel after the $n^{th}$ processing vessel has been inserted into the collector. Magnified view 1010, which is a cross-section taken along the line IX-IX, shows an $n^{th}$ displacement fluid 1012 in an $n^{th}$ processing vessel 1014 and the clearing fluid 1002 and the buffy coat 802 in the primary vessel 702.

Returning to FIG. 6, in block 614, system is centrifuged to collect a fraction or sub-fraction and the nth processing vessel is removed. In block 616, the operator determines whether or not the desired fraction or sub-fraction is obtained in each respective processing vessel. When the desired fraction or sub-fraction is obtained, the process may stop as shown in block 618, though the process may continue until all fractions or sub-fractions are obtained. When the desired fraction or sub-fractions is not yet obtained, the process restarts at block 612. Each collected sub-fraction may include at least a portion of the target material, no target material, or both target and non-target material.

The processing vessels may also include a processing solution to effect a change on the respective sub-fractions. Two or more processing vessels and respective displacement fluids may be used depending on the number of fractions or sub-fractions desired for separation and collection. Each successive displacement fluid is denser than the preceding displacement fluid. Furthermore, the displacement fluid to collect the target material has a density greater than the density of the desired target material; for example, the displacement fluid may have a density that is approximately 0.0001 to approximately 0.1 $g/cm^3$ greater than the density of the desired target material. Similarly, each successive fraction or sub-fraction is denser than the preceding fraction or sub-fraction. Once collected, the consecutive sub-fractions may be analyzed, such as for diagnostic, prognostic, research purposes, to determine components characteristics (i.e. a complete blood count), how those characteristics change over time, or the like.

Figure 10G:
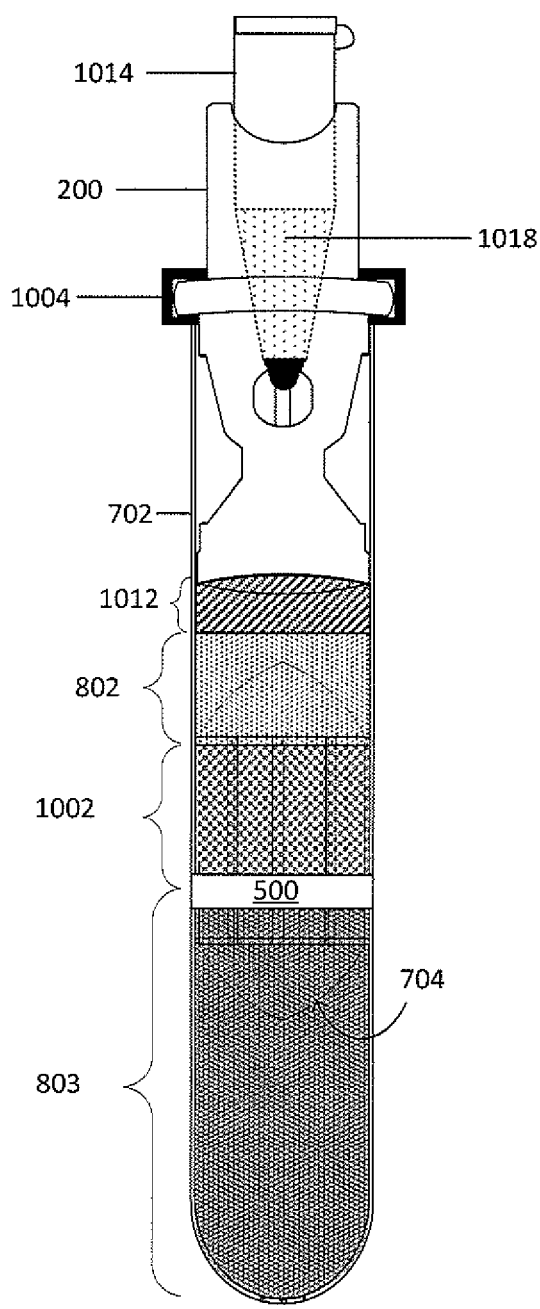

FIG. 10F shows the collector-processing vessel system and the primary vessel 702 undergoing centrifugation. Magnified view 1016, which is a cross-section view taken along the line X-X, shows a snapshot of the exchange of fluids between the primary vessel 702 and the processing vessel 1014. As the clearing fluid 1002, having a greater density than the buffy coat 802, moves down in the primary vessel 702, the buffy coat 802 is cleared from the float 704. As the $n^{th}$ displacement fluid 1012, having a density greater than a first sub-fraction 1018 of the buffy coat 802 but less than the clearing fluid 1002 and the remainder of the buffy coat 802, flows from the processing vessel 302 into the primary vessel 702, the first sub-fraction 1018 moves upwards within the primary vessel 702 through the concave opening 222 and the cannula 214, and into the $n^{th}$ processing vessel 1014. As shown in FIG. 10G, the first sub-fraction 1018 is in the $n^{th}$ processing vessel 1014, while the $n^{th}$ displacement fluid 1012 and the clearing fluid 1002 are in the primary vessel 702. N may be greater than or equal to 1.

The $n^{th}$ processing vessel 1014 including the first sub-fraction 1018 may then be removed from the collector 200 to undergo further processing, analysis, storage, or the like. After removing the nth processing vessel 1014, a processing solution may be added, though the processing solution may have already been in the processing vessel prior to retrieval of the target material. The processing vessel may be shaken, such as by a vortex mixer. The processing solution (not shown), having been added before shaking either in liquid form, in a dissolvable casing, or in a breakable casing, may then mix with the buffy coat to effect a transformation and form a buffy coat-processing solution mixture. The buffy coat-processing solution mixture may then be dispensed onto a substrate, such as a microscope slide.

Subsequent processing vessels and displacement fluids may be used to collect additional sub-fractions of the buffy coat 802 until all sub-fractions are collected or until the desired sub-fraction is collected. Though sequential density fractionation is described as being performed with a float and a sealing ring, sequential density fractionation may be performed without a float, a sealing ring, or both. The following is an example method for performing sequential density fractionation:

1. Add blood and float to tube.
2. Centrifuge to effect a density-based separation of the blood (i.e. plasma, Buffy coat, and red blood cells).

3. Apply sealing ring around the tube and float at a bottom end of the float; clamp.
4. Remove plasma.
5. Add clearing fluid which has a density greater than the density of the target material.
6. Insert collector-processing vessel system, a first processing vessel including a first displacement fluid having a first density.
7. Re-centrifuge.
8. Remove the first processing vessel which now includes a first sub-fraction of the Buffy coat less dense than the first displacement fluid.
9. Insert a second processing vessel into the collector, the second processing vessel including a second displacement fluid having a second density which is greater than the first displacement fluid and less than the clearing fluid.
10. Re-centrifuge.
11. Remove the second processing vessel which now includes a second sub-fraction of the Buffy coat less dense than the second displacement fluid and denser than both the first displacement fluid and the first sub-fraction.
12. Repeat steps 9-11 using successively denser displacement fluids so as to collect successively denser sub-fractions until all desired sub-fractions are obtained.

In other words:
1. inserting an $(n-y)^{th}$ processing vessel into a cavity within the collector,
2. adding an $(n-y)^{th}$ displacement fluid to the $(n-y)^{th}$ processing vessel, the $(n-y)^{th}$ displacement fluid;
3. centrifuging the primary vessel, the collector, and the $(n-y)^{th}$ processing vessel, the $(n-y)^{th}$ displacement fluid to flow into the primary vessel via the collector to displace an $(n-y)^{th}$ sub-fraction of the suspension from the primary vessel into the $(n-y)^{th}$ processing vessel through the collector via the cannula;
4. removing the $(n-y)^{th}$ processing vessel including the $(n-y)^{th}$ sub-fraction from the collector.

For example, n may be any number greater than or equal to 1 and y may be any number greater than or equal to 0, such as n=2 and y=1. Furthermore, n may be the total number of sub-fractions desired and y=(n−1-number of sub-fractions already collected). Furthermore, an $(n+1)^{th}$ sub-fraction does not include any target material.

After retrieving the target material, the target material may be placed on a substrate for imaging and detection (and subsequent storage for archival purposes). At least one portion of the detected target material may then be removed from the substrate, such as by picking, to undergo further analysis. The isolated target material may be deposited into a PCR tube, a well of a well plate, a slide, or any appropriate substrate or vessel for performing the further analysis. Alternatively, the target material may remain within the processing vessel for storage or analysis purposes.

The target material may be analyzed using any appropriate molecular analysis method or technique, such as extracellular and intracellular analysis including intracellular protein labeling, chromogenic staining, nucleic acid analysis, including, but not limited to, DNA arrays, expression arrays, protein arrays, and DNA hybridization arrays; in situ hybridization ("ISH"—a tool for analyzing DNA and/or RNA, such as gene copy number changes); polymerase chain reaction ("PCR"); reverse transcription PCR; or branched DNA ("bDNA"—a tool for analyzing DNA and/or RNA, such as mRNA expression levels) analysis. Fetal material may undergo further processing to test for such fetal abnormalities including, but not limited to, chromosomal abnormalities (e.g. fetal aneuploidy, Down syndrome, trisomy 13, trisomy 18, or a sex chromosome abnormality, such as Turner syndrome), smaller sub-chromosomal abnormalities, gender testing, mutational analysis, and rhesus blood type testing. Additionally, fetal material may undergo expression analysis, for example, for placental function, including pre-eclampsia.

These techniques may require fixation, permeabilization, and isolation (such as by a cell picker) of the target material prior to analysis. Some of the intracellular proteins which may be labeled include, but are not limited to, cytokeratin ("CK"), actin, Arp2/3, coronin, dystrophin, FtsZ, myosin, spectrin, tubulin, collagen, cathepsin D, ALDH, PBGD, Akt1, Akt2, c-myc, caspases, survivin, $p27^{kip}$, FOXC2, BRAF, Phospho-Akt1 and 2, Phospho-Erk1/2, Erk1/2, P38 MAPK, Vimentin, ER, PgR, PI3K, pFAK, KRAS, ALKH1, Twist 1, Snail1, ZEB1, Fibronectin, Slug, Ki-67, M30, MAGEA3, phosphorylated receptor kinases, modified histones, chromatin-associated proteins, and MAGE. To fix, permeabilize, or label, fixing agents (such as formaldehyde, formalin, methanol, acetone, paraformaldehyde, or glutaraldehyde), detergents (such as saponin, polyoxyethylene, digitonin, octyl β-glucoside, octyl β-thioglucoside, 1-S-octyl-β-D-thioglucopyrano side, polysorbate-20, CHAPS, CHAPSO, (1,1,3,3-Tetramethylbutyl)phenyl-polyethylene glycol or octylphenol ethylene oxide), or labeling agents (such as fluorescently-labeled antibodies, enzyme-conjugated antibodies, Pap stain, Giemsa stain, or hematoxylin and eosin stain) may be used. Examples of suitable antibodies for fetal material may include, but is not limited to, INSL4, MMP14, MCAM, KCNQ4, CLDN6, F3, Mouse Anti-Trophoblast protein Monoclonal Antibody, annexin IV, HLA-G, FACE1 (Novus), SLC1A5 (Chemicon-International), CAP-18 (Abeam), ARMCX3 (Novus), OR11H4 (Abeam), CLCN6 (Santa Cruz), Human placental lactogen, Folate binding protein, HCG (human chorionic gonadotropin), Placental alkaline phosphatase, CD147, CD71, CD35, and CD47.

A solution containing a fluorescent probe may be used to label the target material, thereby providing a fluorescent signal for identification and characterization. The solution containing the fluorescent probe may be added to the suspension before the suspension is added to the vessel, after the suspension is added to the vessel but before centrifugation, or after the suspension has undergone centrifugation. The fluorescent probe includes a fluorescent molecule bound to a ligand. The target material may have a number of different types of surface markers. Each type of surface marker is a molecule, such an antigen, capable of attaching a particular ligand, such as an antibody. As a result, ligands can be used to classify the target material and determine the specific type of target materials present in the suspension by conjugating ligands that attach to particular surface markers with a particular fluorescent molecule. Examples of suitable fluorescent molecules include, but are not limited to, quantum dots; commercially available dyes, such as fluorescein, FITC ("fluorescein isothiocyanate"), R-phycoerythrin ("PE"), Texas Red, allophycocyanin, Cy5, Cy7, cascade blue, DAPI ("4',6-diamidino-2-phenylindole"), Hoechst, and TRITC ("tetramethylrhodamine isothiocyanate"); combinations of dyes, such as CY5PE, CY7APC, and CY7PE; and synthesized molecules, such as self-assembling nucleic acid structures. Many solutions may be used, such that each solution includes a different type of fluorescent molecule bound to a different ligand. Furthermore, a nucleus of the target material may have a different size than the nucleuses of the non-target material. Determining nuclear size may aid in differentiating between target and non-target material.

The density of the target material may be increased (such as by attaching a weight to the target material or by having the target material absorb or ingest the weight) or may be decreased (such as by attaching a buoy to the target material or by having the target material absorb or ingest the buoy). The weight or the buoy may be bound to a ligand. The target material may have a number of different types of surface markers. Each type of surface marker is a molecule, such as an antigen, capable of attaching a particular ligand, such as an antibody. As a result, ligands can be selected to attached specifically to the target material to alter the density of the target material. Examples of suitable weights and/or buoys include, but are not limited to beads composed of metal, glass, ceramic, plastic, or combinations thereof. Alternatively, the weight or buoy may be attached to a non-target material to change the density of the non-target material to obtain a purer sample of the target material. Alternatively, the density of the target material may be changed by altering or changing the state of the target material. For example, an immune cell may be activated, thereby causing a change in the density of the activated immune cells. The change in density may occur before collection of the target material into the processing vessel or after collection of the target material into the processing vessel.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments are presented by way of examples for purposes of illustration and description. They are not intended to be exhaustive of or to limit this disclosure to the precise forms described. Many modifications and variations are possible in view of the above teachings. The embodiments are shown and described in order to best explain the principles of this disclosure and practical applications, to thereby enable others skilled in the art to best utilize this disclosure and various embodiments with various modifications as are suited to the particular use contemplated. It is intended that the scope of this disclosure be defined by the following claims and their equivalents:

We claim:

1. A method for collecting target material from a sample, the method comprising the steps of:
    inserting a collector into an open end of a primary vessel that contains the sample;
    inserting an $n^{th}$ processing vessel into a cavity within the collector,
    adding an $n^{th}$ displacement fluid to the $n^{th}$ processing vessel, the $n^{th}$ displacement fluid having a density greater than an $n^{th}$ sub-fraction of a fraction of the sample, the $n^{th}$ sub-fraction including at least a portion of the target material; and
    centrifuging the primary vessel, the collector, and the $n^{th}$ processing vessel, the $n^{th}$ displacement fluid to flow into the primary vessel via a cannula of the collector to displace the $n^{th}$ sub-fraction from the primary vessel into the $n^{th}$ processing vessel via the cannula of the collector.

2. The method of claim 1, wherein $n^{th}$ is equal to or greater than $1^{st}$.

3. The method of claim 1, further comprising the steps of:
    inserting an $(n-y)^{th}$ processing vessel into the cavity within the collector;
    adding an $(n-y)^{th}$ displacement fluid to the $(n-y)^{th}$ processing vessel, the $(n-y)^{th}$ displacement fluid having a density greater than an $(n-y)^{th}$ sub-fraction of a fraction of the sample including at a least a portion of the target material;
    centrifuging the primary vessel, the collector, and the $(n-y)^{th}$ processing vessel, the $(n-y)^{th}$ displacement fluid to flow into the primary vessel via the cannula of the collector to displace the $(n-y)^{th}$ sub-fraction of the suspension from the primary vessel into the $(n-y)^{th}$ processing vessel through the collector via the cannula of the collector; and
    removing the $(n-y)^{th}$ processing vessel including the $(n-y)^{th}$ sub-fraction from the collector,
    wherein all of the steps involving the $(n-y)^{th}$ processing vessels are repeated until the $n^{th}$ processing vessel is reached,
    wherein n is the total number of sub-fractions desired,
    wherein y is (n−1-number of sub-fractions already collected), and
    wherein y is greater than 0.

4. The method of claim 3, wherein at least one of the sub-fractions includes the target material.

5. The method of claim 3, wherein at least one of the sub-fractions does not include the target material.

6. The method of claim 3, wherein the $(n-y)^{th}$ displacement fluid has a density that is approximately 0.0001 to approximately 0.1 g/cm$^3$ greater than the $(n-y)^{th}$ sub-fraction.

7. The method of claim 3, wherein an $(n+1)^{th}$ sub-fraction does not include any target material.

8. The method of claim 3, wherein the fraction is buffy coat and wherein the sub-fractions are different portions of the buffy coat.

9. The method of claim 3, wherein at least one of the sub-fractions includes target material and non-target material.

10. The method of claim 3, wherein the $(n-y)^{th}$ displacement fluid is selected from the group consisting of: a solution of colloidal silica particles coated with polyvinylpyrrolidone, a polysaccharide solution, iodixanol, an organic solvent, a liquid wax, an oil, a gas, olive oil, mineral oil, silicone oil, immersion oil, mineral oil, paraffin oil, silicon oil, fluorosilicone, perfluorodecalin, perfluoroperhydrophenanthrene, perfluorooctylbromide, organic solvents, 1,4-Dioxane, acetonitrile, ethyl acetate, tert-butanol, cyclohexanone, methylene chloride, tert-Amyl alcohol, tert-Butyl methyl ether, butyl acetate, hexanol, nitrobenzene, toluene, octanol, octane, propylene carbonate, tetramethylene sulfones, ionic liquids, a polymer-based solution, a surfactant, a perfluoroketone, perfluorocyclopentanone, perfluorocyclohexanone, a fluorinated ketone, a hydrofluoroether, a hydrofluorocarbon, a perfluorocarbon, a perfluoropolyether, silicon, a silicon-based liquid, phenylmethyl siloxane, and combinations thereof.

11. The method of claim 1, wherein the target material is selected from the group consisting of fetal material, at least one circulating tumor cell, at least one circulating endothelial cell, at least one spirochete, at least one immune cell, at least one exosome, and at least one malaria-inducing agent.

12. The method of claim 1, wherein the target material is fetal material and the fetal material is any biological material that is present in a pregnant female as a result of the pregnancy.

13. The method of claim 12, wherein the target material is at least one trophoblast, nucleated red blood cell, fetal red blood cell, fetal white blood cell, fetal nucleus, fetal DNA, or fetal RNA.

14. The method of claim 12, further comprising the step of testing for at least one fetal abnormality.

15. The method of claim 1, wherein the fraction is buffy coat and wherein the sub-fraction is a portion of the buffy coat.

16. The method of claim 1, wherein the sub-fraction includes target material and non-target material.

17. The method of claim 1, wherein at least one analyte of the target material undergoes molecular analysis.

18. The method of claim 1, wherein at least one analyte of the target material is isolated from the remainder of the target material.

19. The method of claim 1, wherein the $n^{th}$ displacement fluid is selected from the group consisting of: a solution of colloidal silica particles coated with polyvinylpyrrolidone, a polysaccharide solution, iodixanol, an organic solvent, a liquid wax, an oil, a gas, olive oil, mineral oil, silicone oil, immersion oil, mineral oil, paraffin oil, silicon oil, fluorosilicone, perfluorodecalin, perfluoroperhydrophenanthrene, perfluorooctylbromide, organic solvents, 1,4-Dioxane, acetonitrile, ethyl acetate, tert-butanol, cyclohexanone, methylene chloride, tert-Amyl alcohol, tert-Butyl methyl ether, butyl acetate, hexanol, nitrobenzene, toluene, octanol, octane, propylene carbonate, tetramethylene sulfones, ionic liquids, a polymer-based solution, a surfactant, a perfluoroketone, perfluorocyclopentanone, perfluorocyclohexanone, a fluorinated ketone, a hydrofluoroether, a hydrofluorocarbon, a perfluorocarbon, a perfluoropolyether, silicon, a silicon-based liquid, phenylmethyl siloxane, and combinations thereof.

20. The method of claim 1, wherein the $n^{th}$ displacement fluid has a density that is approximately 0.0001 to approximately 0.1 g/cm$^3$ greater than the $n^{th}$ sub-fraction.

* * * * *